(12) United States Patent  (10) Patent No.: US 7,502,649 B2
Ben-Haim et al.  (45) Date of Patent: Mar. 10, 2009

(54) GASTROINTESTINAL METHODS AND APPARATUS FOR USE IN TREATING DISORDERS

(75) Inventors: Shlomo Ben-Haim, Caesarea (IL); Shai Policker, Moshav zur Moshe (IL); Ricardo Aviv, Haifa (IL); Ofer Glasberg, Haifa (IL)

(73) Assignee: Metacure Ltd., Hamilton (BM)

( * ) Notice: Subject to any disclaimer, the term of this patent is extended or adjusted under 35 U.S.C. 154(b) by 0 days.

(21) Appl. No.: 10/561,491

(22) PCT Filed: Jun. 20, 2004

(86) PCT No.: PCT/IL2004/000550

§ 371 (c)(1),
(2), (4) Date: Feb. 28, 2007

(87) PCT Pub. No.: WO2004/112563

PCT Pub. Date: Dec. 29, 2004

(65) Prior Publication Data

US 2007/0179556 A1  Aug. 2, 2007

Related U.S. Application Data

(60) Provisional application No. 60/480,208, filed on Jun. 20, 2003, provisional application No. 60/480,205, filed on Jun. 20, 2003.

(51) Int. Cl.
*A61N 1/08* (2006.01)
(52) U.S. Cl. ............... 607/40; 607/2; 607/41; 607/62; 607/133; 600/546; 600/547; 600/593
(58) Field of Classification Search ............ 607/2, 607/40–41, 62, 133; 600/546–547, 593
See application file for complete search history.

(56) References Cited

U.S. PATENT DOCUMENTS 3,411,507 A  11/1968 Wingrove (Continued)

FOREIGN PATENT DOCUMENTS

EP  0057048  8/1982

(Continued)

OTHER PUBLICATIONS

Rocca, A.S., et al. "Role of the Vagus Nerve in Mediating Proximal Nutrient-Induced Glucagon-Like Peptide-1 Secretion." Endocrinology, 140(4), pp. 1687-1694. 1999.*

(Continued)

*Primary Examiner*—Carl H Layno
*Assistant Examiner*—Deborah Malamud
(74) *Attorney, Agent, or Firm*—William H. Dippert; Eckert Seamans Cherin & Mellott

(57) ABSTRACT

A method is provided for detecting a change in posture of a subject. An electrical impedance is measured between two or more sites on a stomach (20) of the subject, and an impedance signal is generated responsive thereto. The change in posture is detected by performing a posture analysis of the impedance signal. A method is also provided for treating a subject. The method includes applying an electrical signal to a site of the subject selected from the list consisting of: a colon (402) of the subject, and a distal small intestine (408) of the subject. The signal is configured to stimulate cells of the subject to increase secretion of glucagon-like-peptide-1 (GLP-1) or PYY, or to decrease secretion of ghrelin, in order to treat the subject.

41 Claims, 10 Drawing Sheets

U.S. PATENT DOCUMENTS

| | | |
|---|---|---|
| 3,516,412 A | 6/1970 | Ackerman |
| 3,737,579 A | 6/1973 | Boldue |
| 4,000,745 A | 1/1977 | Goldberg et al. |
| 4,010,758 A | 3/1977 | Rockland et al. |
| 4,133,315 A | 1/1979 | Berman et al. |
| 4,177,818 A | 12/1979 | De Pedro |
| 4,235,246 A | 11/1980 | Weiss |
| 4,280,503 A | 7/1981 | Ackerman |
| 4,313,448 A | 2/1982 | Stokes |
| 4,357,946 A | 11/1982 | Dutcher et al. |
| 4,378,023 A | 3/1983 | Trabucco |
| 4,416,267 A | 11/1983 | Garren et al. |
| 4,452,254 A | 6/1984 | Goldberg et al. |
| 4,485,805 A | 12/1984 | Foster, Jr. |
| 4,592,339 A | 6/1986 | Kuzmak |
| 4,823,808 A | 4/1989 | Clegg et al. |
| 4,975,682 A | 12/1990 | Kerr et al. |
| 5,074,868 A | 12/1991 | Kuzmak |
| 5,101,814 A | 4/1992 | Palti |
| 5,103,804 A | 4/1992 | Abele et al. |
| 5,105,812 A | 4/1992 | Corman |
| 5,188,104 A | 2/1993 | Wernicke et al. |
| 5,190,041 A | 3/1993 | Palti |
| 5,226,429 A | 7/1993 | Kuzmak |
| 5,234,454 A | 8/1993 | Bangs |
| 5,247,938 A | 9/1993 | Silverstein et al. |
| 5,263,480 A | 11/1993 | Wernicke et al. |
| 5,314,463 A | 5/1994 | Camps et al. |
| 5,368,028 A | 11/1994 | Palti |
| 5,423,872 A | 6/1995 | Cigaina |
| 5,449,368 A | 9/1995 | Kuzmak |
| 5,514,175 A | 5/1996 | Kim et al. |
| 5,540,730 A | 7/1996 | Terry et al. |
| 5,551,425 A | 9/1996 | Essen-Moller |
| 5,601,604 A | 2/1997 | Vincent |
| 5,690,691 A | 11/1997 | Chen et al. |
| 5,704,368 A | 1/1998 | Asano et al. |
| 5,716,385 A | 2/1998 | Mittal et al. |
| 5,741,211 A | 4/1998 | Renirie et al. |
| 5,792,210 A | 8/1998 | Wamubu et al. |
| 5,795,304 A | 8/1998 | Sun et al. |
| 5,836,994 A | 11/1998 | Bourgeois |
| 5,837,006 A | 11/1998 | Ocel et al. |
| 5,861,014 A | 1/1999 | Familoni |
| 5,868,141 A | 2/1999 | Ellias |
| 5,919,216 A | 7/1999 | Houben et al. |
| 5,938,669 A | 8/1999 | Klaiber et al. |
| 5,979,449 A | 11/1999 | Steer |
| 5,991,649 A | 11/1999 | Garfield et al. |
| 5,995,872 A | 11/1999 | Bourgeois |
| 6,026,326 A | 2/2000 | Bardy |
| 6,041,258 A | 3/2000 | Cigaina et al. |
| 6,067,991 A | 5/2000 | Forsell |
| 6,083,249 A | 7/2000 | Familoni |
| 6,091,992 A | 7/2000 | Bourgeois |
| 6,092,528 A | 7/2000 | Edwards |
| 6,093,167 A | 7/2000 | Houben et al. |
| 6,104,955 A | 8/2000 | Bourgeois |
| 6,115,635 A | 9/2000 | Bourgeois |
| 6,129,685 A | 10/2000 | Howard |
| 6,132,372 A | 10/2000 | Essen-Moller |
| 6,135,978 A | 10/2000 | Houben |
| 6,216,045 B1 | 4/2001 | Black et al. |
| 6,243,607 B1 | 6/2001 | Mintchev |
| 6,249,697 B1 | 6/2001 | Asano et al. |
| 6,261,280 B1 | 7/2001 | Houben et al. |
| 6,334,073 B1 | 12/2001 | Levine |
| 6,363,937 B1 | 4/2002 | Hovda et al. |
| 6,381,495 B1 | 4/2002 | Jenkins |
| 6,405,732 B1 | 6/2002 | Edwards |
| 6,411,842 B1 | 6/2002 | Cigaina et al. |
| 6,415,178 B1 | 7/2002 | Ben-Haim et al. |
| 6,427,089 B1 | 7/2002 | Knowlton |
| 6,449,511 B1 | 9/2002 | Mintchev |
| 6,454,699 B1 | 9/2002 | Forsell |
| 6,535,764 B2 | 3/2003 | Imran et al. |
| 6,571,127 B1 | 5/2003 | Ben-Haim et al. |
| 6,572,542 B1 | 6/2003 | Houben et al. |
| 6,584,348 B2 | 6/2003 | Glukhovsky |
| 6,591,137 B1 | 7/2003 | Fischell et al. |
| 6,600,953 B2 | 7/2003 | Flesler et al. |
| 6,606,523 B1 | 8/2003 | Jenkins |
| 6,609,025 B2 | 8/2003 | Barrett et al. |
| 6,612,983 B1 | 9/2003 | Marchal |
| 6,652,444 B1 | 11/2003 | Ross |
| 6,658,297 B2 | 12/2003 | Loeb |
| 6,684,104 B2 | 1/2004 | Gordon |
| 6,735,477 B2 | 5/2004 | Levine |
| 6,745,079 B2 | 6/2004 | King |
| 6,754,536 B2 | 6/2004 | Swoyer et al. |
| 6,826,428 B1 | 11/2004 | Chen et al. |
| 6,832,114 B1 | 12/2004 | Whitehurst |
| 6,852,110 B2 | 2/2005 | Roy et al. |
| 6,853,862 B1 | 2/2005 | Marchal et al. |
| 6,869,431 B2 | 3/2005 | Maguire et al. |
| 6,876,885 B2 | 4/2005 | Swoyer et al. |
| 6,895,279 B2 | 5/2005 | Loeb et al. |
| 6,918,906 B2 | 7/2005 | Long |
| 6,939,349 B2 | 9/2005 | Fleischman et al. |
| 6,947,792 B2 | 9/2005 | Ben-Haim et al. |
| 6,952,613 B2 | 10/2005 | Swoyer et al. |
| 7,043,295 B2 | 5/2006 | Starkebaum |
| 7,054,690 B2 | 5/2006 | Imran |
| 7,076,305 B2 | 7/2006 | Imran et al. |
| 7,076,306 B2 | 7/2006 | Marchal et al. |
| 2001/0011543 A1 | 8/2001 | Forsell |
| 2002/0026141 A1 | 2/2002 | Houben |
| 2002/0103424 A1 | 8/2002 | Swoyer et al. |
| 2002/0161414 A1 | 10/2002 | Flesler et al. |
| 2003/0045919 A1 | 3/2003 | Swoyer et al. |
| 2003/0055464 A1 | 3/2003 | Darvish |
| 2003/0066536 A1 | 4/2003 | Forsell |
| 2003/0144708 A1 | 7/2003 | Starkebaum |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0220678 A1 | 11/2003 | Tronnes et al. |
| 2004/0044376 A1 | 3/2004 | Flesler et al. |
| 2004/0059393 A1 | 3/2004 | Policker et al. |
| 2004/0088023 A1 | 5/2004 | Imran et al. |
| 2004/0107004 A1 | 6/2004 | Levine et al. |
| 2004/0147816 A1 | 7/2004 | Policker et al. |
| 2004/0158138 A1 | 8/2004 | Kilcoyne et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer et al. |
| 2004/0236316 A1 | 11/2004 | Danitz et al. |
| 2004/0249421 A1 | 12/2004 | Harel et al. |
| 2005/0020965 A1 | 1/2005 | Rioux et al. |
| 2005/0021101 A1 | 1/2005 | Chen et al. |
| 2005/0055038 A1 | 3/2005 | Kelleher et al. |
| 2005/0065505 A1 | 3/2005 | Ryan |
| 2005/0075654 A1 | 4/2005 | Kelleher |
| 2005/0090873 A1 | 4/2005 | Imran |
| 2005/0107829 A1 | 5/2005 | Edwards et al. |
| 2005/0143784 A1 | 6/2005 | Imran |
| 2005/0183732 A1 | 8/2005 | Edwards |
| 2005/0192615 A1 | 9/2005 | Torre et al. |
| 2005/0203500 A1 | 9/2005 | Saadat et al. |
| 2005/0209653 A1 | 9/2005 | Herbert et al. |
| 2005/0222638 A1 | 10/2005 | Foley et al. |
| 2006/0142803 A1 | 6/2006 | Mintchev |
| 2006/0173238 A1 | 8/2006 | Starkebaum |

| | | |
|---|---|---|
| 2006/0247718 A1 | 11/2006 | Starkebaum |

FOREIGN PATENT DOCUMENTS

| | | |
|---|---|---|
| EP | 0129483 | 12/1984 |
| EP | 1036545 | 9/2000 |
| EP | 1 447 052 | 8/2004 |
| EP | 144705 | 6/2005 |
| JP | 2003/319945 | 11/2003 |
| JP | 2003319945 | 11/2003 |
| WO | WO 94/01172 | 1/1994 |
| WO | WO 97/25098 | 7/1997 |
| WO | WO 98/10830 | 3/1998 |
| WO | WO 99/03533 | 1/1999 |
| WO | WO 00/53257 | 9/2000 |
| WO | WO 01/41671 | 6/2001 |
| WO | WO 01/66183 | 9/2001 |
| WO | WO 01/83019 | 11/2001 |
| WO | WO 01/91854 | 12/2001 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 2004/043280 | 5/2004 |
| WO | WO 2004/066903 | 8/2004 |
| WO | WO 2004/069330 | 8/2004 |
| WO | WO 2004/091361 | 10/2004 |
| WO | WO 2004/096337 | 11/2004 |
| WO | WO 2004/112563 | 12/2004 |
| WO | WO 2005/007232 | 1/2005 |
| WO | WO 2005/007237 | 1/2005 |
| WO | WO 2005/009288 | 2/2005 |
| WO | WO 2005/016181 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2006/035446 | 4/2006 |
| WO | WO 2006/118790 | 11/2006 |

OTHER PUBLICATIONS

Jaremko, et al., "Advances toward the implantable artificial pancreas for treatment of diabetes", Diabetes Care, 21(3), Mar. 1998.

Lamb F.S. et al., "Cyclosporine augments reactivity of isolated blood vessels", Life Sciences, 40, pp. 2571-2578, 1987.

Johansson B. et al., "Static and dynamic components in the vascular myogenic response to passive changes in length as revealed by electrical and mechanical recordings from the rat portal vein", Circulation Research, 36, pp. 76-83, 1975.

Zelcer E. et al., "Spontaneous electrical activity in pressurized small mesenteric arteries", Blood Vessels, 19, pp. 301-310, 1982.

Schobel H.P. et al., "Preeclampsia—a state of sympathetic overactivity", New England Journal of Medicine, 335, pp. 148-1485, 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity. II. Mitochondrial variables", American Journal of Physiology, 274(4 Pt 1): C1174-1184, Apr. 1998.

Gut R. et al., "High-precision EMG signal decomposition using communication techniques", IEEE transactions on signal processing, 48(9), pp. 2487-2494, Sep. 2000.

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.

T Vilsboll and Associates, Research design and methods, Diabetes, vol. 50, Mar. 2001, pp. 610-613.

Jeannie F. Todd, et al., "Subcutaneous glucagons-like peptide-1 improves postprandial glycaemic control over 3-week period in patients with early type 2 diabetes", Clinical Science (1998) 95, 325-329.

Daniel J. Drucker, "Development of glucagon-like peptide-1-based pharmaceuticals as therapeutic agents for the treatment of diabetes", Current Pharmaceutical Design, 2001, 7, 1399-1412.

Meda et al., Quarterly J. Exper. Physiol. 69:719-735 (1984).

Eddiestone et al., J. Membrane Biol. 77:1-141 (1984).

U.S. Appl. No. 10/273,263.

Yamada, "Effects of drugs on electromechanical activities of the stomach and duodenum of conscious dogs", Nippon Heikatsukin Gakkai Zasshi. Feb. 1983;19(1):25-35. (abstract only).

Shemerovskii KA, "Effect of feeding on the activity of duodenal smooth muscle in dogs", Biull Eksp Biol Med. Oct. 1978;86(10):394-7. (Abstract only).

\* cited by examiner

GASTROINTESTINAL METHODS AND APPARATUS FOR USE IN TREATING DISORDERS

CROSS-REFERENCES TO RELATED APPLICATION

The present application is a U.S. National Stage filing of Patent Cooperation Treaty ("PCT") Patent Application Ser. No. PCT/1L2004/000550, filed Jun. 20, 2004, which in turn claim priority to U.S. Provisional Patent Applications Ser. Nos. 60/480,208 and 60/480,205, both filed Jun. 20, 2003, which are hereby incorporated by reference herein in their entirety.

The present patent application is related to a PCT application filed on even date herewith, entitled, "Hepatic device for treatment, eating detection, and glucose level detection," which is assigned to the assignee of the present application and is incorporated herein by reference.

FIELD OF THE INVENTION

The present invention relates generally to treatment of metabolic conditions, and specifically to invasive techniques and apparatus for treating metabolic and behavioral conditions.

BACKGROUND OF THE INVENTION

Invasive treatments for obesity are often recommended for patients with a body mass index (mass/height$^2$ [kg/m$^2$]) which is greater than 35 or 40. For such patients, their weight is commonly associated with increased risk of heart disease, diabetes, and arthritis. Preferably, the invasive treatments are accompanied by changes in lifestyle, such as improved eating habits and an appropriate exercise regimen.

U.S. patent application Ser. No. 09/734,358 to Flesler et al., which published as US Patent Application Publication 2002/0161414, and which is assigned to the assignee of the present patent application and is incorporated herein by reference, describes apparatus for treating a condition such as obesity. The apparatus includes a set of one or more electrodes, which are adapted to be applied to one or more respective sites in a vicinity of a body of a stomach of a patient. A control unit is adapted to drive the electrode set to apply to the body of the stomach a signal, configured such that application thereof increases a level of contraction of muscle tissue of the body of the stomach, and decreases a cross-sectional area of a portion of the body of the stomach for a substantially continuous period greater than about 3 seconds.

PCT Publication WO 02/082968 to Policker et al., which is assigned to the assignee of the present application and is incorporated herein by reference, describes a diet evaluation gastric apparatus, which detects when a patient swallows, and detects the type and amount of matter ingested. The apparatus includes electrodes adapted to be coupled to the fundus and antrum of the patient and to measure electrical and mechanical activity therein, and a control unit to analyze such electrical and mechanical activity and optionally apply electrical energy to modify the activity of tissue of the patient.

U.S. Pat. No. 5,690,691 to Chen et al., which is incorporated herein by reference, describes a gastric pacemaker for treating obesity and other conditions. The pacemaker includes multiple electrodes which are placed at various positions on the gastrointestinal (GI) tract, and which deliver phased electrical stimulation to pace peristaltic movement of material through the GI tract.

U.S. Pat. No. 6,243,607 to Mintchev et al., which is incorporated herein by reference, describes a gastro-intestinal electrical pacemaker, including multiple electrodes which are arranged around a portion of the GI tract. The electrodes stimulate smooth muscle so that local contractions of the portion of the GI tract are artificially propagated therethrough, in order to facilitate a partial emptying of the portion. Preferably, the local contractions are artificially propagated by phase locking or time shifting the electrical stimulus, which is applied to the smooth muscle circumferentially about the portion at two or more locations.

U.S. Pat. No. 5,423,872 to Cigaina, which is incorporated herein by reference, describes apparatus for applying electrical pulses to the distal gastric antrum of a patient, so as to reduce the motility of the stomach and to thereby treat obesity or another condition.

U.S. Pat. No. 5,231,988 to Wernicke et al., which is incorporated herein by reference, describes techniques for treating and controlling diabetes and other systemic pancreatic endocrine disorders attributable to abnormal levels of secretion of endogenous insulin An electrical stimulator implanted into or worn external to the patient's body is adapted, when activated, to generate a programmable electrical waveform for application to electrodes implanted on the vagus nerve of the patient. The electrical waveform is programmed using parameter values selected to stimulate or inhibit the vagus nerve to modulate the electrical activity thereof to increase or decrease secretion of natural insulin by the patient's pancreas. The stimulator is selectively activated manually by the patient in response to direct measurement of blood glucose or symptoms, or is activated automatically by programming the activation to occur at predetermined times and for predetermined intervals during the circadian cycle of the patient. Alternatively, the automatic activation is achieved using an implanted sensor to detect the blood glucose concentration, and is triggered when the patient's blood glucose concentration exceeds or falls below a predetermined level depending on whether diabetes or hypoglycemia is being treated.

U.S. Pat. Nos. 5,188,104 and 5,263,480 to Wernicke et al., which are incorporated herein by reference, describe a method for stimulating the vagus nerve of a patient so as to alleviate an eating disorder.

U.S. Pat. Nos. 6,104,955, 6,091,992, and 5,836,994 to Bourgeois, U.S. Pat. No. 6,026,326 to Bardy, and U.S. Pat. No. 3,411,507 to Wingrove, which are incorporated herein by reference, describe the application of electrical signals to the GI tract to treat various physiological disorders.

PCT Patent Publication WO 99/03533 to Ben-Haim et al., entitled, "Smooth muscle controller," and U.S. patent application Ser. No. 09/481,253 in the national phase thereof, both of which are assigned to the assignee of the present patent application and are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion.

U.S. Pat. No. 6,317,631 to Ben-Haim et al., which is assigned to the assignee of the present patent application and is incorporated herein by reference, describes methods for modifying the force of contraction of a heart chamber by applying an ETC signal to the heart.

U.S. Pat. No. 5,716,385 to Mittal et al., which is incorporated herein by reference, describes a crural diaphragm pacemaker for treating gastroesophageal reflux. The pacemaker includes one or more electrodes which are placed in contact with the crural diaphragm, either by implantation or by connecting the electrodes to the skeletal muscles of the crural diaphragm through the skin. During spontaneous intermittent relaxations of the diaphragm, the electrodes stimulate the skeletal muscles of the crural diaphragm, in order to cause contraction of the lower esophageal sphincter.

U.S. Pat. No. 6,535,764 to Imran et al., which is incorporated herein by reference, describes techniques for diagnosing and treating gastric disorders. A functional device resides within the patient's stomach and is secured to the stomach wall by an attachment device. The functional device may be a sensor for sensing various parameters of the stomach or stomach environment, or may be a therapeutic delivery device. The functional device in one embodiment comprises stimulating electrodes for gastric electrical stimulation.

U.S. Pat. No. 4,696,288 to Kuzmak et al., which is incorporated herein by reference, describes calibrating apparatus adapted to be inserted into and proceeded within the stomach of human body. The calibrating apparatus includes a single-lumen tubing terminating in a proximal portion and a distal tip, each of which has an orifice. The single-lumen tubing has a first opening extending therethrough which is located at a selected distance from the proximal portion and a second opening which extends therethrough and which is located a predetermined distance from the distal tip; an elongated, thin-walled sensor having a circular-cross section and a cavity within the interior thereof and which is operatively coupled in a sealing relationship to the distal tip, wherein the thin-walled sensor is capable of having its cross-sectional diameter varied in response to a force applied to the exterior of the sensor to vary the pressure of a fluid within the cavity, and a balloon surrounding the exterior of said single-lumen tubing at the preselected location, which encloses the second opening, and an elongated tubing member which extends through the single-lumen tubing, through the first opening and into communication with the second opening.

U.S. Pat. No. 4,592,339 to Kuzmak et al., which is incorporated herein by reference, describes a gastric band for forming a stoma opening in a stomach for treating morbid obesity. The band is invasively placed around the stomach, and an expandable portion of the band is used to adjust the diameter of the stoma opening.

U.S. Pat. Nos. 5,449,368, 5,226,429, and 5,074,868 to Kuzmak, which are incorporated herein by reference, describe adjustable gastric bands. The size of the stoma opening of the bands can be adjusted by injecting into or removing fluid from an expandable section of the gastric bands.

U.S. Pat. No. 5,601,604 to Vincent, which is incorporated herein by reference, describes a gastric band for placement around the stomach for treating morbid obesity. The inner surface of the band is inflatable through a remote fill port. The band is invasively placed in an encircling position around the stomach by the facile closure of a single fastening means. After the band is fastened around the stomach, a fluid is injected into the inflatable inner surface, thereby constricting the stoma of the stomach.

U.S. Pat. No. 5,658,298 to Vincent et al., which is incorporated herein by reference, describes a tool for tightening a band or ligature having a buckle end and a free end during laparoscopic surgery.

PCT Publication WO 01/83019 to Vincent, which is incorporated herein by reference, describes apparatus and methods for transferring particles and fluids to or from a body of a patient, including inflating a balloon inside the body during surgical procedures to facilitate the identification of anatomical landmarks and to provide guidance for surgical dissections. The apparatus includes an inflation lumen communicating with the balloon, and a transfer lumen in communication with one or more openings. The method permits a surgeon to empty the contents of the stomach, decompress the stomach, inflate the balloon, perform an operation, such as one involving gastric banding or gastric bypass, using the balloon as a landmark, and irrigate the stomach to check for gastric perforations at the end of the surgical procedure.

U.S. Pat. No. 5,938,669 to Klaiber et al., which is incorporated herein by reference, describes an adjustable gastric band for contracting a patient's stomach in order to fight obesity. A gastric band of a known type, implanted around the stomach and including a cavity filled with liquid, is connected by a tube to a control box and a balancing reservoir which are implanted under the skin of the patient. The box contains an electric pump and an electronic control unit capable of communicating by radio with a monitor carried by the patient and with a controller intended for the doctor. The controller can operate the pump by remote control to transfer determined volumes of liquid in a closed circuit from the gastric band to the reservoir or vice versa, to adjust the diameter of a passage in the stomach. The monitor receives and signals alarms from the control box.

U.S. Pat. No. 6,067,991 to Forsell, which is incorporated herein by reference, describes an adjustable gastric band including an elongated non-inflatable restriction member, a forming device for forming the restriction member into at least a substantially closed loop around the stomach or the esophagus to define a restriction opening, and a post-operation non-invasive adjustment device for mechanically adjusting the restriction member in the loop to change the size of the restriction opening.

U.S. Pat. No. 6,210,347 to Forsell, which is incorporated herein by reference, describes a food intake restriction device for forming a stoma opening in the stomach or esophagus of a patient. The device comprises an elongated restriction member to be formed into at least a substantially closed loop defining a restriction opening, and a controllable adjustment device for adjusting the restriction member in the loop to change the size of the restriction opening. The device further comprises a wireless remote control for controlling the adjustment device from outside the body of the patient in a non-invasive manner to assist in treating the patient for morbid obesity.

U.S. Pat. No. 6,460,543 to Forsell, which is incorporated herein by reference, describes a food intake restriction device for forming a stoma opening in the stomach or esophagus of a patient. The device comprises an elongated restriction member forming an expandable and contractible cavity formed into an at least substantially closed loop defining a restriction opening, the size of which is reduced upon expansion of the cavity and increased upon contraction of the cavity. A reservoir containing a predetermined amount of hydraulic fluid and connected to the cavity of the restriction member, and a hydraulic operation device for distributing fluid from the reservoir to the cavity to expand the cavity and for distributing fluid from the cavity to the reservoir to contract the cavity, are also implanted in a patient with morbid obesity and operated from outside the body of the patient in a non-invasive manner. A non-inflatable restriction member may alternatively be used, and hydraulically adjusted.

U.S. Pat. No. 6,453,907 to Forsell, which is incorporated herein by reference, describes an adjustable gastric band that includes an energy transmission device for wireless transmission of energy of a first form from outside the body of the patient. The band is adjusted in response to a second energy form different than the first form to vary the restricted stoma. An energy transfer device is implanted in the patient for transferring energy of the first form transmitted by the energy transmission device into energy of the second form.

U.S. Pat. No. 6,454,699 to Forsell, which is incorporated herein by reference, describes food intake restriction apparatus that includes a restriction device implanted in a patient, which engages the stomach or esophagus to form an upper pouch and a restricted stoma opening in the stomach or esophagus. The apparatus includes a source of energy external to the body of the patient, and a control device for releasing wireless energy from the source of energy from outside the body. The released wireless energy is used in connection with the operation of the restriction device, to enlarge it to allow food passage, or to contract it to substantially prevent food passage. The restriction device optionally includes at least one implanted sensor for sensing at least one physical parameter of the patient, in which case the control device may control the restriction device in response to signals from the sensor.

US Patent Application Publication 2003/0066536 to Forsell, which is incorporated herein by reference, describes food intake restriction apparatus, including an operable restriction device implanted in a patient and engaging the stomach or esophagus to form a restricted stoma opening in the stomach or esophagus. The apparatus includes a source of energy for energizing the restriction device, and a control device for releasing energy from the source of energy from outside the body of the patient. The released energy is used in connection with the operation of the restriction device to vary the size of the stoma opening to allow or substantially prevent the passage of food therethrough. The restriction apparatus optionally includes a pressure sensor for directly or indirectly sensing the pressure in the stomach. The control device may control the restriction device in response to signals from the pressure sensor.

US Patent Application Publication 2001/0011543 to Forsell, which is incorporated herein by reference, describes apparatus for treating morbid obesity or heartburn and reflux disease, including an elongated restriction member formed in a substantially closed loop around a stomach or esophagus of a human to form a stoma opening in the stomach or esophagus. The size of the stoma opening is adjustable by an implanted adjustment device. A control device is utilized to control the adjustment device, in order to either reduce or enlarge the size of the stoma opening, for example in response to the time of the day. A sensor, such as a pressure or position sensor, is surgically implanted in the body of the human so that the sensor may either directly or indirectly sense a physical parameter of the human, such as the pressure in the stomach or the human's orientation with respect to the horizontal. If in response to sensing by the sensor it is determined by the control device that a significant change in the physical parameter has occurred, then the control device controls the adjustment device to either reduce or enlarge the size of the stoma opening.

PCT Publication WO 01/41671 to Cigaina, which is incorporated herein by reference, describes a removable gastric band for controlling obesity by allowing control and/or modification of the diameter of a stomach of a patient. The gastric band comprises a closure mechanism, which allows the elongated body to close around a portion of the stomach. The gastric band can be used in conjunction with a gastric electrostimulator, and is therefore described as being potentially useful for inducing forced slimming in the initial phase of treatment for morbigenous obesity. Such electrostimulation devices may either be incorporated into the removable gastric band or located at a distance from the removable gastric band.

European Patent Application Publication 1 036 545 A2 to Moshe, which is incorporated herein by reference, describes a gastric band for attaching around a circumference of a stomach of a patient, so as to define the diameter of the stomach opening. The band comprises outer and inner surfaces, wherein the inner surface engages the stomach, and at least the outer surface is formed by an elongated member substantially non-extendable along a longitudinal axis thereof. A through-going opening is made in the elongated member and is located so as to define an end portion of the band having a predetermined length. An opposite end portion of the band is shaped so as to be insertable into the through-going opening, for adjusting a desired inner diameter of the band in its closed operating position and fastening the opposite end portion to the outer surface of the band.

U.S. Pat. No. 6,511,490 to Robert, which is incorporated herein by reference, describes a gastric banding device for implantation within a person for the treatment of morbid obesity. The gastric banding device includes an inflatable band portion dimensioned to encircle the stomach, and an inflation conduit operable for conducting a percutaneously injected inflation fluid into the band portion. The band portion is a toroidal member having a head end with first fastening means thereon and a tail end having second fastening means thereon and an inflatable shell therebetween. The outer surface of the toroidal shell in reinforced with a non-extensible, biocompatible material which serves to limit outward expansion of the shell when an inflation fluid is injected thereinto. The inner, stomach-contacting surface of the shell has a layer of an open-cell elastomeric foam affixed thereto and integral therewith. In operation, when the band is placed in an encircling relationship with the stomach, the first and second fastening means on the ends of the shell are engaged in locking relationship. An inflation fluid is injected into the shell by means of a subcutaneously implanted injection port that is in fluid communication with the inflation conduit. As the shell expands inwardly, it constricts and compartmentalizes the stomach.

U.S. Pat. No. 6,547,801 to Dargent et al., which is incorporated herein by reference, describes an implantable gastric constriction device comprising a constriction member forming a ring in its operational configuration. The constriction member includes a flexible band, of which the two ends are adjacent to one another in the operational configuration, and a means for actuating the constriction member, characterized in that, in cooperation, on the one hand, at least one end of the flexible band includes a tractile element for moving such end relative to the other end, generating a radial deformation of the constriction member, and, on the other hand, the actuating means comprises a member for pulling the tractile element.

U.S. Pat. No. 5,259,399 to Brown, which is incorporated herein by reference, describes a method and apparatus for causing weight loss in obese patients by occupying a segment of the stomach volume using a variable volume bladder filled with fluid. The bladder is inserted into the upper part of the stomach including the fundus through a percutaneous endoscopic gastrostomy tube, which was non-surgically placed to create a permanent channel to the stomach. The inserted bladder is filled and emptied using a filling system for pumping fluid in and out of the bladder according to a predetermined scheme. The filling system comprises a reversible pump, a two-way valve connected to the filling tube, an electronic control means for automatically controlling the action of the filling system, and a battery. The electronic control means is connected to a plurality of sensors placed on the body of the patient to detect digestion cycle and hemodynamic parameters. The electronic control means collects information detected by the sensors, governs the filling system according to the obtained information and predetermined operation scheme, and records times and volumes of the fluid transferred through the two-way valve.

U.S. Pat. No. 5,234,454 to Bangs, which is incorporated herein by reference, describes a method for controlling the body weight of a patient. The method includes inserting a percutaneous intragastric balloon catheter into the stomach of the patient through a gastrostomy tract. The intragastric balloon catheter comprises elongated shaft means having first and second ends, a first inflatable balloon carried proximal to the first end, and a second inflatable balloon carried proximal to the first inflatable balloon, the second balloon having a lesser inflated volume than the first balloon. The balloon catheter further comprises first and second inflation lumens, first and second inflation ports communicating respectively with the first and second inflation lumens and the first and second balloons, which ports are carried by the second end, and a drainage lumen passing between said first and second ends. The method continues by inflating the first and second balloons within the patient, partially filling the stomach to provide satiety.

U.S. Pat. No. 4,416,267 to Garren et al., which is incorporated herein by reference, describes a stomach insert for treating obesity in humans by reducing the stomach volume. The insert comprises a flexible torus-shaped inflatable balloon having a central opening extending therethrough. At least a portion of the balloon has a self-sealing substance to facilitate puncture thereof with a needle for inflating the balloon and sealing of the puncture upon removal of the needle.

U.S. Pat. No. 6,454,785 to De Hoyos Garza, which is incorporated herein by reference, describes a percutaneous intragastric balloon catheter for the treatment of obesity. The balloon is non-surgically placed in the stomach, and is collocated by percutaneous endoscopic gastrostomy (PEG). The balloon includes a valve for regulating the amount of fluid introduced or evacuated from the balloon.

INAMED Corporation (Santa Barbara, Calif.) manufactures and markets the LAP-BAND® System, an FDA-approved adjustable and reversible gastric band for treatment of obesity.

Glucagon-like-peptide-1 (GLP-1) is a known modulator of insulin secretion in the early phases of a meal and a mediator of satiety. In response to ingestion of a meal, GLP-1 is secreted into the blood by L-cells mainly located in the colon and distal small intestine. Administration of GLP-1, either subcutaneously or peripherally, has been shown to improve glycemic control, partially by restoring the first-phase insulin response and suppressing glucagon, and is therefore considered a potential treatment for obesity and Non-Insulin Dependent Diabetes Mellitus (NIDDM).

Todd J F et al., in an article entitled, "Glucagon-like peptide-1 (GLP-1): a trial of treatment in non-insulin-dependent diabetes mellitus," Eur J Clin Invest 27 (6):533-6 (1997), which is incorporated herein by reference, write that "GLP-1 has the advantages of both suppressing glucagon secretion and delaying gastric emptying." They conclude, "GLP-1 improves glycaemic control even in the absence of an insulinotropic effect and is a potential treatment for NIDDM."

U.S. Pat. No. 6,191,102 to DiMarchi et al., which is incorporated herein by reference, describes pharmaceutical compositions comprising a glucagon-like peptide-1 compound for reducing body weight and treating obesity. The compositions are peripherally administered.

The following articles, which are incorporated herein by reference, may be of interest:

Gutniak M K et al., "Subcutaneous injection of the incretin hormone glucagon-like peptide 1 abolishes postprandial glycemia in NIDDM," Diabetes Care 17(9):1039-44 (1994)

Robertson M D et al., "The influence of the colon on postprandial glucagon-like peptide 1 (7-36) amide concentration in man," J Endocrinol 161(1):25-31 (1999)

Schirra J et al., "Mechanisms of the antidiabetic action of subcutaneous glucagon-like peptide-1 (7-36) amide in non-insulin dependent diabetes mellitus," J Endocrinol 156(1): 177-86 (1998)

Todd J F et al., "Subcutaneous glucagon-like peptide-1 improves postprandial glycaemic control over a 3-week period in patients with early type 2 diabetes," Clin Sci (Lond) 95(3):325-9 (1998)

Vilsboll T et al., "Reduced postprandial concentrations of intact biologically active glucagon-like peptide 1 in type 2 diabetic patients," Diabetes 50(3):609-13 (2001)

SUMMARY OF THE INVENTION

In some embodiments of the present invention, gastric control apparatus for treating obesity comprises a controllable mechanical and/or electrical gastric device for modifying a volume of a stomach of a patient, and a set of one or more sensors for sensing physiological parameters indicative of ingestion by the patient. The gastric device is adapted to reduce the stomach volume below an initial stomach volume, so as to cause a sensation of satiety felt by the patient, and therefore generally reduce the patient's appetite. A control unit is adapted to receive one or more signals from the sensors, to analyze the signals, and to drive the gastric device to modify the stomach volume in real-time responsive to the analysis.

In some embodiments of the present invention, the gastric device comprises a gastric band, adapted to be placed around the stomach, and to be tightened and loosened in real time, responsive to signals received from the control unit. Tightening of the band causes a narrowing of the stomach, thereby reducing the volume of the stomach. In other embodiments, the gastric device comprises a gastric balloon, adapted to be placed in the stomach, and to be inflated and deflated in real time, responsive to signals received from the control unit. Inflation of the balloon reduces the effective volume of the stomach, and, directly or indirectly, induces distention of the stomach wall. In still other embodiments, the gastric device comprises a set of one or more electrodes which are applied to the stomach, and apply an electrical signal as to modify a contraction pattern of some of the stomach's muscles, in order to reduce the cross-sectional area of a portion of the stomach In some embodiments of the present invention, the control unit is adapted to drive the gastric device to reduce the stomach volume during eating by the patient. The control unit employs an eating detection algorithm to detect the eating, responsive to changes in one or more sensed parameters. The eating detection algorithm typically utilizes one or both of the following sub-algorithms for detecting eating: an impedance sub-algorithm and an electrical slow wave sub-algorithm. An increase in impedance is generally caused by stomach distension resulting from eating. Typically, impedance measurements using electrodes placed on or near the fundus detect eating somewhat earlier than do impedance measurements using electrodes placed on or near the antrum. A decrease in electrical activity in the antrum is generally caused by digestive activity resulting from the stomach filling with food.

The impedance eating detection sub-algorithm typically uses a slow-reacting formula to calculate and remove a baseline impedance value. The formula is slow reacting in order to reduce the effect of noise on the calculation of the baseline impedance value. The sub-algorithm then processes raw real-time impedance measurements by applying both a high-pass filter and a low-pass filter to the measurements, in order to effect a band-pass filter. The resulting processed impedance value is compared to a threshold value, and if found to be greater, is interpreted as an indication of eating. For some applications, the impedance sub-algorithm interprets sudden substantial changes in impedance as indications of changes in posture of the patient, rather than as indications of eating. At least one value in the filter (e.g., the baseline impedance value) is modified in response to the posture-change indication, such that the filter, during this time, operates in a non-linear fashion. Such interpretations of sudden substantial changes in impedance may reduce false detections of eating caused by changes in posture.

The electrical slow-wave eating detection sub-algorithm analyzes real-time electrical measurements, in order to detect electrical events indicative of eating by the patient. The sub-algorithm calculates the average time difference (lag) between successive recent electrical events, and interprets an average greater than a threshold value as indicative of eating. (In general, a decrease in the rate of electrical slow-waves in the antrum occurs during digestive activity caused by the stomach filling with food.) For some applications, the sub-algorithm also compares the average time difference to an upper threshold value, and interprets an average greater than the upper threshold value as indicative of a false eating detection rather than a real eating event. Such false positives may be caused by an occasional lack of detection of a slow wave by the sensors, which erroneously increases the average time difference.

In some embodiments of the present invention, a colonic stimulation system comprises a control unit and one or more electrodes, which are adapted to be applied to respective sites in a vicinity of a colon or a distal small intestine of a patient. The control unit drives the electrodes to apply electrical signals to the sites, and configures the signals to stimulate L-cells or other target tissue, which, responsive to such stimulation, increase secretion of glucagon-like-peptide-1 (GLP-1). Such secretion of GLP-1 generally improves glycemic control of the patient, and therefore serves to treat patients suffering from insulin-resistance-related conditions, such as obesity, NIDDM, heart disease, and hypertension, or healthy patients considered at risk for such conditions. For some applications, the colonic stimulation system further comprises an eating detection unit, and the control unit is configured to drive the electrodes to apply the signals responsive to a detection of eating.

The inventors hypothesize that stimulation of the colon or the distal portion of the small intestine, as described herein, may induce up-regulation of insulin sensitivity in some types of cells. This up-regulation may occur by means of (a) an indirect response to the stimulation, and/or (b) secretion of a hormone in response to the stimulation.

There is therefore provided, in accordance with an embodiment of the present invention, a method for detecting a change in posture of a subject, the method including:
  measuring an electrical impedance between two or more sites on a stomach of the subject, and generating an impedance signal responsive thereto; and
  analyzing the impedance signal in order to detect the change in posture.

For some applications, the method includes:
  further analyzing the impedance signal in order to detect an indication of potential eating by the subject; and
  interpreting the indication of potential eating as an indication of eating only if the change in posture has not been detected.

There is further provided, in accordance with an embodiment of the present invention, a method for detecting eating by a subject, the method including:
  measuring an electrical impedance between two or more sites on a stomach of the subject, and generating an impedance signal responsive thereto;
  analyzing the impedance signal in order to detect a change in posture of the subject;
  further analyzing the impedance signal in order to detect an indication of potential eating by the subject; and
  interpreting the indication of potential eating as an indication of eating only if the change in posture has not been detected.

There is yet further provided, in accordance with an embodiment of the present invention, a method for treating a subject, including:
  applying an electrical signal to a colon or a distal small intestine of the subject; and
  configuring the signal to stimulate cells to increase secretion of glucagon-like-peptide-1 (GLP-1), in order to treat the subject.

In an embodiment, the method includes detecting eating by the subject, and applying the electrical signal includes applying the signal responsive to detecting the eating.

There is also provided, in accordance with an embodiment of the present invention, a method for detecting a change in posture of a subject, the method including:
  measuring an electrical impedance between two or more sites on a stomach of the subject, and generating an impedance signal responsive thereto; and
  detecting the change in posture by performing a posture analysis of the impedance signal.

For some applications, the method includes detecting an indication of potential eating by the subject by performing an eating analysis of the impedance signal; and responsive to the posture analysis, interpreting the impedance signal as indicative of eating.

There is further provided, in accordance with an embodiment of the present invention, a method for detecting eating by a subject, the method including:
  measuring an electrical impedance between two or more sites on a stomach of the subject, and generating an impedance signal responsive thereto;
  detecting a change in posture of the subject by performing a posture analysis of the impedance signal;
  detecting an indication of potential eating by the subject by performing an eating analysis of the impedance signal; and responsive to the posture analysis, interpreting the impedance signal as indicative of the eating.

For some applications, detecting the change in posture includes interpreting a sudden, substantial change in the impedance signal as indicative of the change in posture. Alternatively or additionally, detecting the change in posture includes interpreting a sudden, sustained change in the impedance signal as indicative of the change in posture.

For some applications, the method includes providing insulin to a blood circulation of the subject responsively to detecting the eating. For some applications, the method includes providing cholecystokinin to a blood circulation of the subject responsively to detecting the eating. For some applications, the method includes applying an electrical signal to a pancreas of the subject responsively to detecting the eating. For some applications, the method includes modulating insulin secretion by applying an electrical signal to a vagus nerve of the subject responsively to detecting the eating.

For some applications, detecting the indication of potential eating includes analyzing an electrical measurement of the stomach, and, responsive to the analysis, determining whether an electrical event indicative of a slow wave has occurred.

In an embodiment, detecting the indication of potential eating includes calculating a baseline value of the impedance signal. For some applications, interpreting includes modifying the baseline value responsively to the posture analysis. For some applications, calculating the baseline value includes using a slow-reacting formula to calculate the baseline value.

For some applications, detecting the indication of potential eating includes applying a low-pass filter to the impedance signal. For some applications, detecting the indication of potential eating includes applying a high-pass filter to the impedance signal. For some applications, interpreting includes modifying at least one value in the filter responsively to detecting the change in posture.

In an embodiment, the method includes reducing a volume of the stomach responsively to the indication of eating. For some applications, reducing the volume of the stomach includes tightening a gastric band around the stomach. Alternatively or additionally, reducing the volume of the stomach includes inflating a gastric balloon in the stomach. Further alternatively or additionally, reducing the volume of the stomach includes applying an electrical signal to the stomach, and configuring the electrical signal to modify a contraction pattern of one or more muscles of the stomach.

There is still further provided, in accordance with an embodiment of the present invention, a method for treating a subject, including:
applying an electrical signal to a site of the subject selected from the list consisting of: a colon of the subject, or and a distal small intestine of the subject; and
configuring the signal to stimulate cells of the subject to increase secretion of glucagon-like-peptide-1 (GLP-1), in order to treat the subject.

In an embodiment, the cells include L-cells, and configuring the signal includes configuring the signal to stimulate the L-cells to increase the secretion of the GLP-1.

For some applications, the site includes the colon, and applying the signal includes applying the signal to the colon. Alternatively or additionally, the site includes the distal small intestine, and applying the signal includes applying the signal to the distal small intestine.

For some applications, the method includes selecting a subject suffering from a condition selected from the list consisting of: obesity, NIDDM, heart disease, and hypertension, and applying the signal includes applying the signal to the site of the selected subject.

For some applications, applying the signal includes applying the signal not responsively to detecting eating by the subject.

For some applications, applying the signal includes applying the signal periodically.

For some applications, configuring the signal includes varying at least one parameter of the signal in real time.

In an embodiment, applying the signal includes applying an excitable tissue control (ETC) signal to the site. For some applications, the method includes sensing natural electrical activity of the site, and applying the ETC signal includes applying the ETC signal responsive to the sensed natural electrical activity.

In an embodiment, configuring the signal includes detecting an occurrence selected from the list consisting of: an occurrence of eating, an occurrence of excessive eating, and an occurrence of an elevated blood glucose level; and responsive to detecting the occurrence, increasing a strength of the signal. For some applications, applying the signal includes applying the signal in bursts of pulses, and increasing the strength of the signal includes increasing a frequency of the pulses in each of the bursts. For some applications, applying the signal includes applying the signal in bursts of pulses, and increasing the strength of the signal includes decreasing a spacing between successive bursts.

In an embodiment, applying the signal includes applying the signal in bursts of pulses. For some applications, configuring the signal includes configuring a spacing between successive bursts to have a duration of between about 1 and about 10 seconds. For some applications, configuring the signal includes configuring a frequency of the pulses within each of the bursts to be between about 1 and about 200 Hz. For some applications, configuring the signal includes configuring a frequency of the pulses within each of the bursts to be between about 5 and about 50 Hz.

For some applications, the method includes detecting eating by the subject, and applying the electrical signal includes applying the signal responsive to detecting the eating. For some applications, applying the signal responsive to detecting the eating includes commencing applying the signal at a time selected from the list consisting of: substantially simultaneously with a commencement of the eating, between about one and about 5 minutes after the commencement of the eating, and between about one and about 5 minutes prior to the commencement of the eating.

For some applications, detecting the eating includes:
measuring an electrical impedance between two or more sites on a stomach of the subject, and generating an impedance signal responsive thereto;
detecting a change in posture of the subject by performing a posture analysis of the impedance signal;
detecting an indication of potential eating by the subject by performing an eating analysis of the impedance signal; and
responsive to the posture analysis, interpreting the impedance signal as indicative of the eating.

For some applications, detecting the eating includes:
measuring an electrical impedance between two or more sites on a stomach of the subject, and generating an impedance signal responsive thereto;
comparing a measure of a sudden, sustained change in the impedance signal to a threshold; and
detecting the eating by analyzing the impedance signal, and responsive to the comparing.

For some applications, detecting the eating includes analyzing an electrical measurement of the stomach, and, responsive to the analysis, determining whether an electrical event indicative of a slow wave has occurred.

There is additionally provided, in accordance with an embodiment of the present invention, a method for treating a subject, including:

applying an electrical signal to a site of the subject selected from the list consisting of: a colon of the subject, and a distal small intestine of the subject; and configuring the signal to perform an action selected from the list consisting of: stimulate cells of the subject to increase secretion of peptide YY (PYY), and inhibit secretion of ghrelin by cells of the subject, in order to treat the subject.

For some applications, the cells include L-cells.

For some applications, the site includes the colon, and applying the signal includes applying the signal to the colon. Alternatively or additionally, the site includes the distal small intestine, and applying the signal includes applying the signal to the distal small intestine.

For some applications, the method includes selecting a subject suffering from a condition selected from the list consisting of: obesity, NIDDM, heart disease, and hypertension, and applying the signal includes applying the signal to the site of the selected subject.

For some applications, applying the signal includes applying the signal not responsively to detecting eating by the subject.

For some applications, applying the signal includes applying the signal periodically.

For some applications, configuring the signal includes varying at least one parameter of the signal in real time.

In an embodiment, applying the signal includes applying an excitable tissue control (ETC) signal to the site. For some applications, the method includes sensing natural electrical activity of the site, and applying the ETC signal includes applying the ETC signal responsive to the sensed natural electrical activity.

In an embodiment, configuring the signal includes:

detecting an occurrence selected from the list consisting of: an occurrence of eating, an occurrence of excessive eating, and an occurrence of an elevated blood glucose level; and responsive to detecting the occurrence, increasing a strength of the signal.

For some applications, applying the signal includes applying the signal in bursts of pulses, and increasing the strength of the signal includes increasing a frequency of the pulses in each of the bursts.

In an embodiment, applying the signal includes applying the signal in bursts of pulses, and increasing the strength of the signal includes decreasing a spacing between successive bursts.

For some applications, applying the signal includes applying the signal in bursts of pulses.

For some applications, configuring the signal includes configuring a spacing between successive bursts to have a duration of between about 1 and about 10 seconds.

For some applications, configuring the signal includes configuring a frequency of the pulses within each of the bursts to be between about 1 and about 200 Hz. For some applications, configuring the signal includes configuring a frequency of the pulses within each of the bursts to be between about 5 and about 50 Hz.

For some applications, the method includes detecting eating by the subject, and applying the electrical signal includes applying the signal responsive to detecting the eating.

For some applications, applying the signal responsive to detecting the eating includes commencing applying the signal at a time selected from the list consisting of: substantially simultaneously with a commencement of the eating, between about one and about 5 minutes after the commencement of the eating, and between about one and about 5 minutes prior to the commencement of the eating.

There is yet additionally provided, in accordance with an embodiment of the present invention, a method for detecting a change in posture of a subject, the method including:

measuring an electrical impedance between two or more sites on tissue of the subject, and generating an impedance signal responsive thereto; and detecting the change in posture by performing a posture analysis of the impedance signal.

For some applications, the method includes:

detecting an indication of potential eating by the subject by performing an eating analysis of the impedance signal; and responsive to the posture analysis, interpreting the impedance signal as indicative of eating.

There is also provided, in accordance with an embodiment of the present invention, a method for detecting eating by a subject, the method including:

measuring an electrical impedance between two or more sites on a stomach of the subject, and generating an impedance signal responsive thereto;

comparing a measure of a sudden, sustained change in the impedance signal to a threshold; and detecting the eating by analyzing the impedance signal, and responsive to the comparing.

For some applications, analyzing the impedance signal includes applying a high-pass filter to the impedance signal. For some applications, analyzing the impedance signal includes comparing a measure of the impedance signal with a threshold. For some applications, analyzing the impedance signal includes applying a low-pass filter to the impedance signal.

For some applications, comparing the measure of the change includes calculating a difference between a current measure of the change and a previous measure of the change, and comparing an absolute value of the difference to the threshold.

For some applications, analyzing the impedance signal includes calculating a baseline value of the impedance signal. For some applications, calculating the baseline value includes using a slow-reacting formula to calculate the baseline value. For some applications, detecting the eating includes resetting the baseline value when the measure is greater than the threshold. For some applications, resetting the baseline value includes adding a current value of the impedance signal to the baseline value.

There is further provided, in accordance with an embodiment of the present invention, apparatus for detecting a change in posture of a subject, including:

two electrodes, adapted for coupling to respective sites on a stomach of the subject; and a control unit, adapted to:

drive a current between the electrodes, measure, responsive to the current, an electrical impedance between the sites, generate an impedance signal responsive to the measured electrical impedance, and detect the change in posture by performing a posture analysis of the impedance signal.

There is still further provided, in accordance with an embodiment of the present invention, apparatus for detecting eating by a subject, including:

two electrodes, adapted for coupling to respective sites on a stomach of the subject; and a control unit, adapted to:
drive a current between the electrodes,
measure, responsive to the current, an electrical impedance between the sites,
generate an impedance signal responsive to the measured electrical impedance,
detect a change in posture of the subject by performing a posture analysis of the impedance signal,
detect an indication of potential eating by the subject by performing an eating analysis of the impedance signal, and
responsive to the posture analysis, interpret the impedance signal as indicative of the eating.

There is additionally provided, in accordance with an embodiment of the present invention, apparatus for treating a subject, including:

at least one electrode, adapted to be coupled to a site of the subject selected from the list consisting of: a colon of the subject, and a distal small intestine of the subject; and a control unit, adapted to drive the at least one electrode to apply an electrical signal to the site, and to configure the signal to stimulate cells of the subject to increase secretion of glucagon-like-peptide-1 (GLP-1), in order to treat the subject.

There is yet additionally provided, in accordance with an embodiment of the present invention, apparatus for treating a subject, including:

at least one electrode, adapted to be coupled to a site of the subject selected from the list consisting of: a colon of the subject, and a distal small intestine of the subject; and a control unit, adapted to drive the at least one electrode to apply an electrical signal to the site, and to configure the signal to perform an action selected from the list consisting of: stimulate cells of the subject to increase secretion of peptide YY (PYY), and inhibit secretion of ghrelin by cells of the subject, in order to treat the subject.

There is also provided, in accordance with an embodiment of the present invention, apparatus for detecting a change in posture of a subject, including:

two electrodes, adapted for coupling to respective sites on tissue of the subject; and a control unit, adapted to:
drive a current between the electrodes,
measure, responsive to the current, an electrical impedance between the sites,
generate an impedance signal responsive to the measured electrical impedance, and
detect the change in posture by performing a posture analysis of the impedance signal.

There is further provided, in accordance with an embodiment of the present invention, apparatus for detecting eating by a subject, including:

two electrodes, adapted for coupling to respective sites on a stomach of the subject; and a control unit, adapted to:
drive a current between the electrodes,
measure, responsive to the current, an electrical impedance between the sites,
generate an impedance signal responsive to the measured electrical impedance,
compare a measure of a sudden, sustained change in the impedance signal to a threshold; and
detect the eating by analyzing the impedance signal, and responsive to the comparing.

The present invention will be more fully understood from the following detailed description of the embodiments thereof, taken together with the drawings, in which:

DETAILED DESCRIPTION OF EMBODIMENTS

Figure 1:
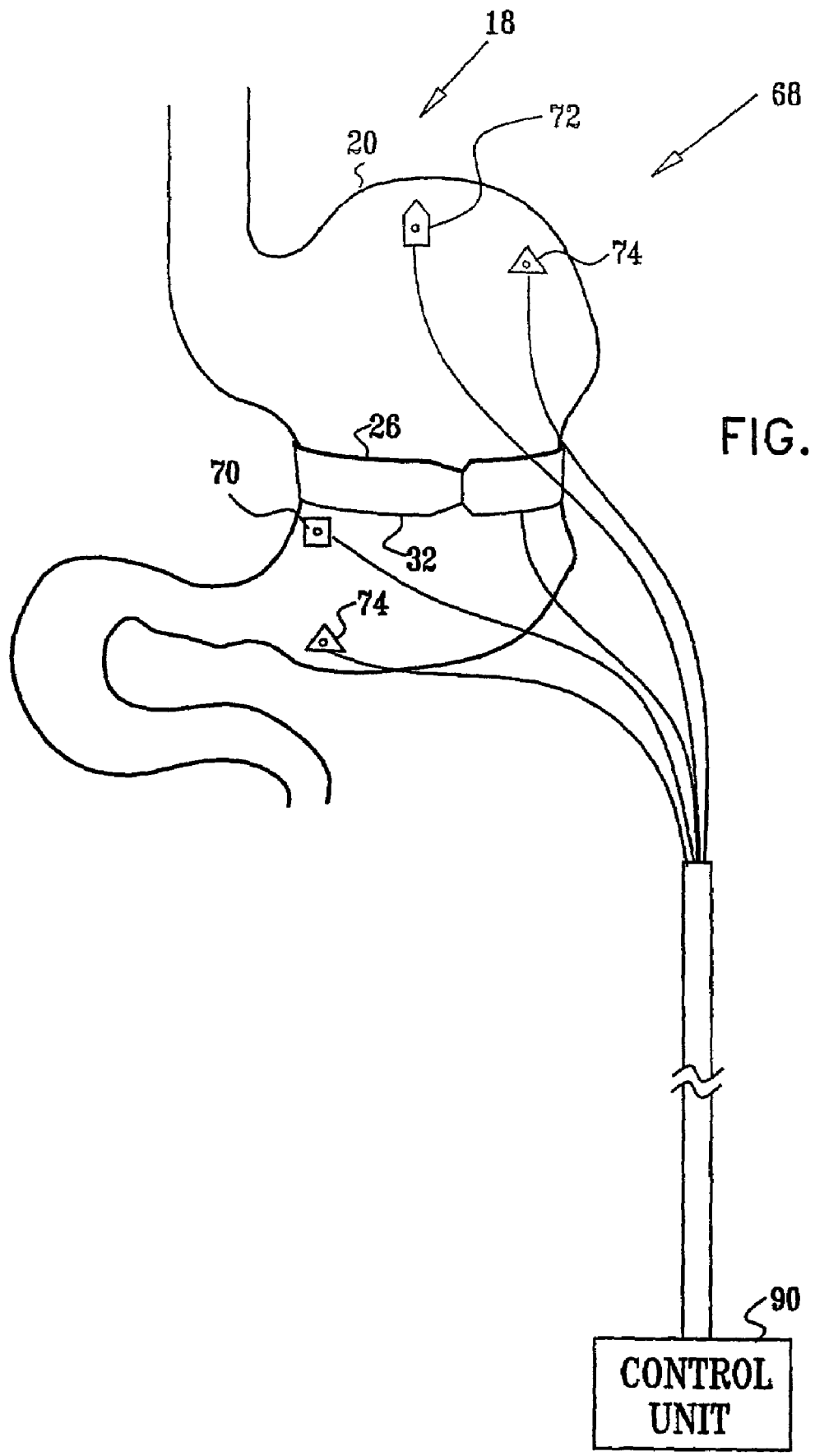
FIG. 1 is a schematic illustration of gastric control apparatus comprising an adjustable gastric band, in accordance with an embodiment of the present invention.
Figure 2:
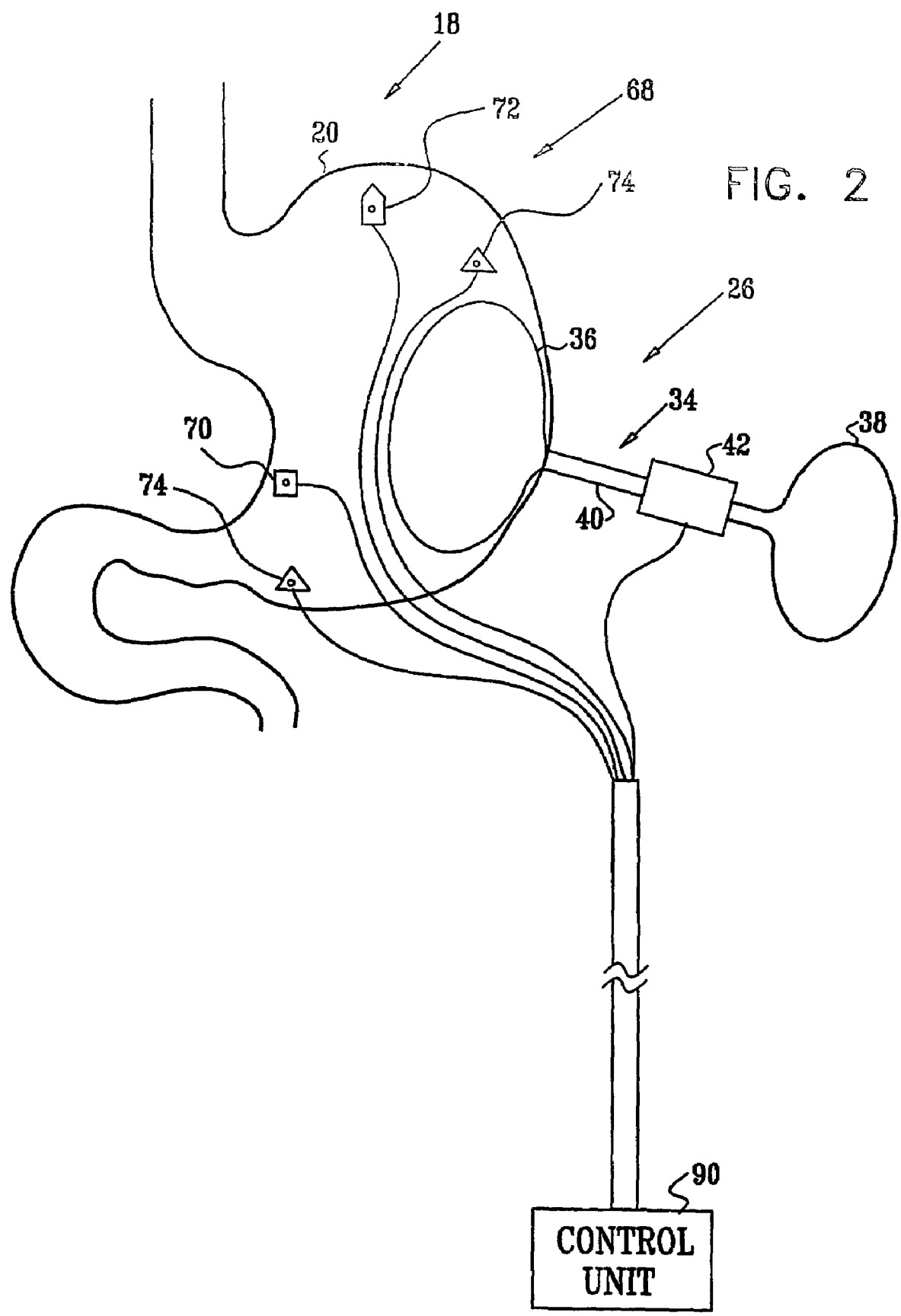
FIG. 2 is a schematic illustration of gastric control apparatus comprising a gastric balloon assembly, in accordance with an embodiment of the present invention.
Figure 3:
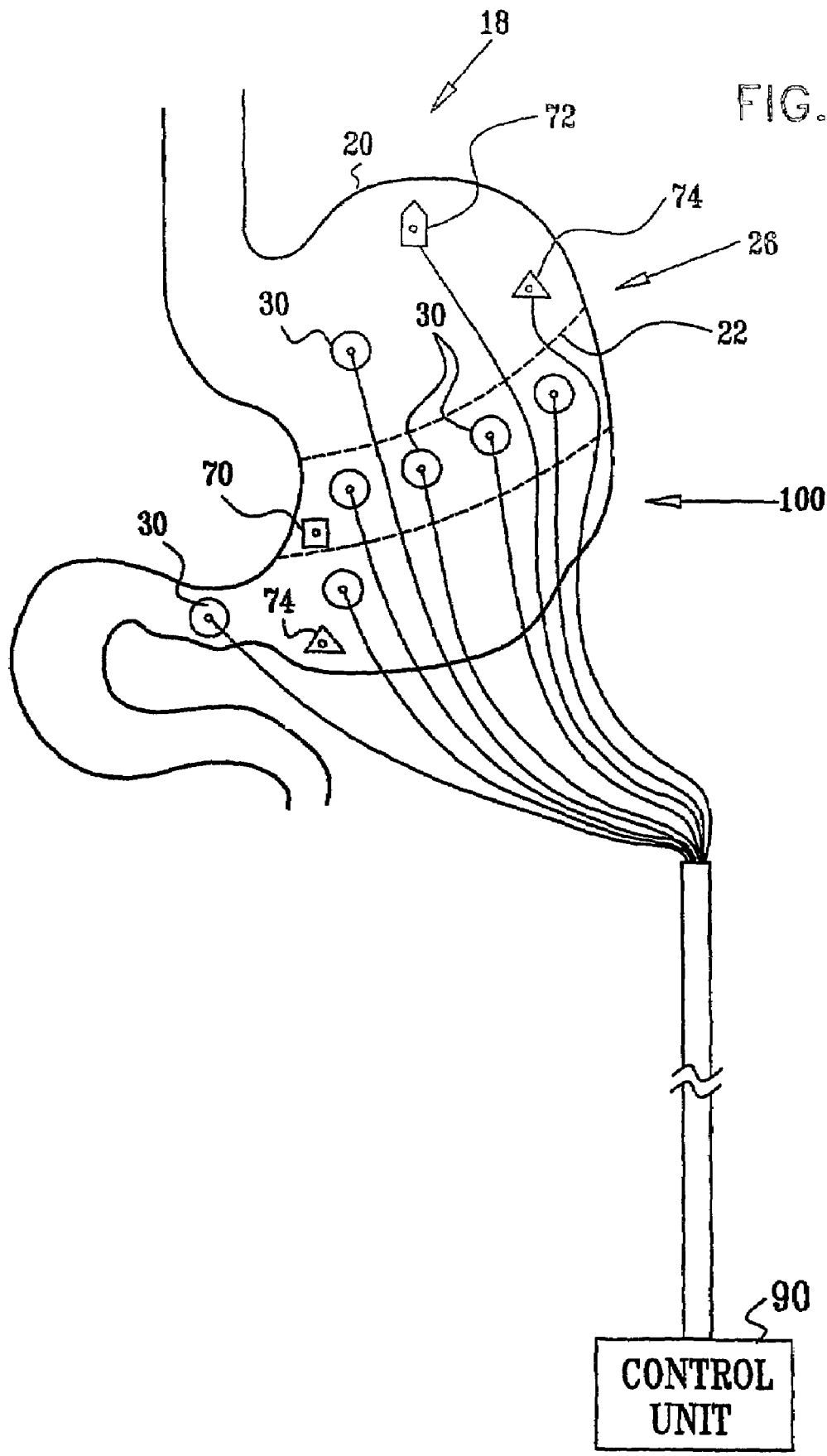
FIG. 3 is a schematic illustration of gastric control apparatus comprising one or more stimulation electrodes, in accordance with an embodiment of the present invention.

Reference is now made to FIGS. 1, 2, and 3, which are schematic illustrations of gastric control apparatus 18, in accordance with respective embodiments of the present invention. Apparatus 18 comprises an implantable or external control unit 90, and a gastric device 26, adapted to mechanically or electrically modify a volume of a stomach 20 of a patient. In the embodiment shown in FIG. 1, gastric device 26 comprises an adjustable gastric band 32, adapted to be placed around stomach 20 and tightened so as to cause a narrowing of stomach 20, thereby reducing the volume of the stomach 20. In the embodiment shown in FIG. 2, gastric device 26 comprises a gastric balloon assembly 34, a balloon 36 of which is adapted to be placed in stomach 20 and inflated so as to reduce the effective volume of stomach 20 (i.e., the volume of the stomach available for holding food before physiological indications of satiety are generated). In the embodiment shown in FIG. 3, gastric device 26 comprises one or more electrodes 100, which are driven by control unit 90 to apply an enhancement signal to respective sites on or in a vicinity of stomach 20, in order to modify a contraction pattern of some of the stomach's muscles so as to reduce the cross-sectional area of a portion of the stomach.

Apparatus 18 typically further comprises a set of one or more sensors 68 for sensing physiological parameters indicative of ingestion by the patient. Sensors 68 may comprise, for example, one or more dedicated local sense electrodes 74, which are typically placed on or in stomach 20, and convey electrical signals to control unit 90 responsive to natural gastric electric activity. Alternatively or additionally, sensors 68 comprise one or more mechanical sensors 70 (e.g., accelerometers, force transducers, strain gauges, or pressure gauges), which are placed on or in stomach 20 and are coupled to control unit 90. Further alternatively or additionally, sensors 68 comprise one or more supplemental sensors 72 (e.g., pH sensors, blood sugar sensors, intragastric pressure sensors and/or sonometric sensors), which are placed on or in the gastrointestinal tract or elsewhere on or in the body of the patient, and are coupled to control unit 90. In an embodiment, one or more of sensors 68 are fixed to a surface of gastric device 26 that comes in contact with tissue of stomach 20, such as the inner surface of gastric band 32 or the outer surface of balloon 36.

Control unit 90 is adapted to receive one or more signals from sensors 68, to analyze the signals, and to drive gastric device 26 to adjust in real-time the magnitude of stomach volume reduction responsive to the analysis. The reduced stomach volume increases the sensation of satiety felt by the patient compared to that which would be felt without such stomach volume reduction, and therefore generally reduces the patient's appetite so as to treat the obesity. Typically, control unit 90 and sensors 68 are permanently or semi-permanently implanted in or coupled to the body of the patient. The number of sensors, as well as the positions thereof, are shown in FIGS. 1-3 by way of example, and other sites on stomach 20 or in a vicinity thereof are appropriate for sensor placement in other applications of the present invention.

Figure 4:
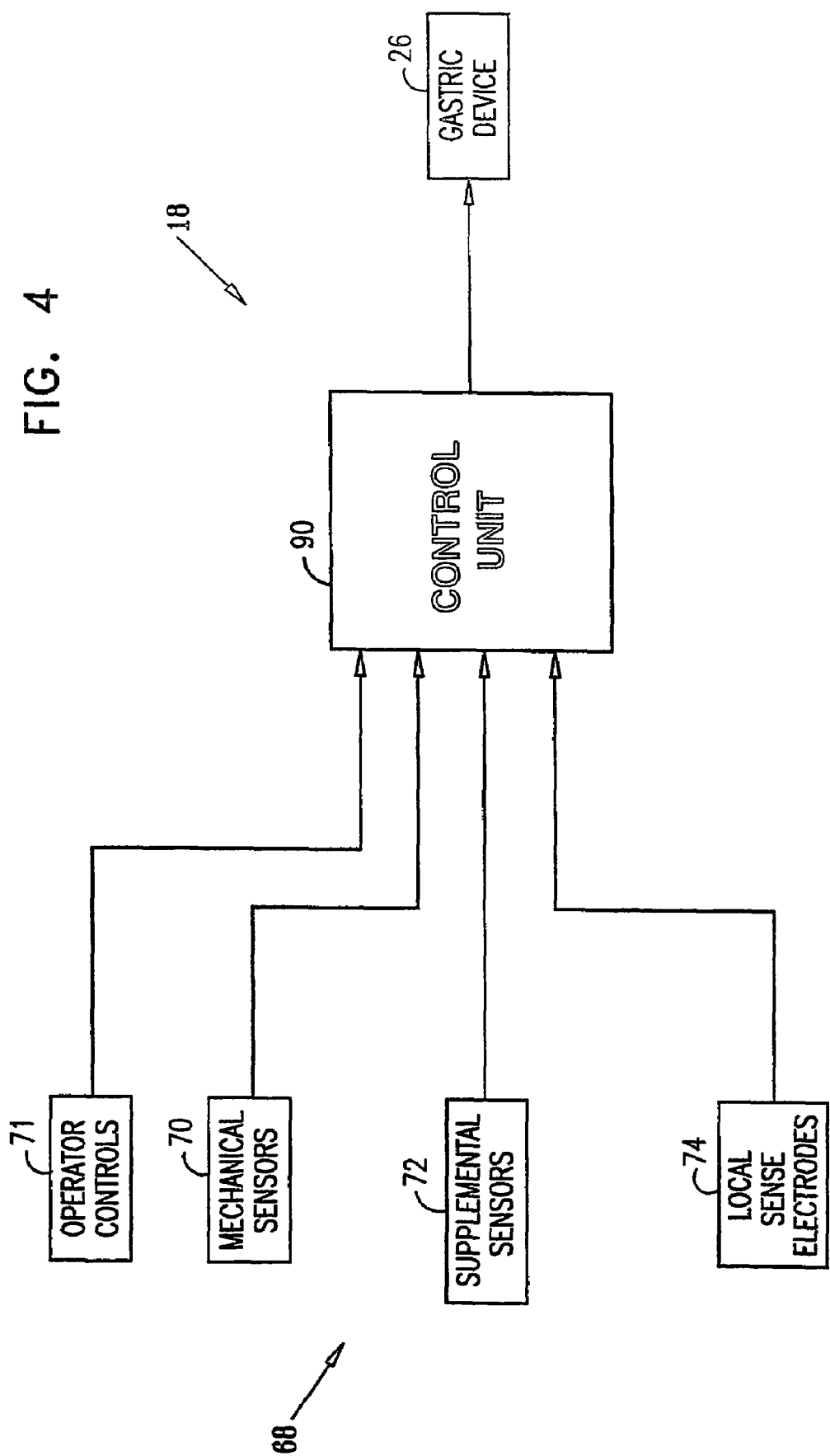
FIG. 4 is a schematic block diagram of gastric control apparatus, in accordance with an embodiment of the present invention.

FIG. 4 is a schematic block diagram of gastric control apparatus 18, in accordance with an embodiment of the present invention. Sensors 68 are typically coupled to provide feedback signals to control unit 90. The feedback signals generally provide control unit 90 with information about various aspects of the present state of the stomach (e.g., empty or full) and the level of activity of the stomach (e.g., indications of current or recent ingestion by the patient), so as to enable control unit 90 to analyze the signals and drive gastric device 26 responsive to the analysis. Typically, the magnitude of stomach volume reduction is adjusted by control unit 90 responsive to the feedback signals in order to yield a desired response, e.g., an indication by mechanical sensors 70 of a desired level of stomach contraction, or an indication by supplemental sensors 72 of maintenance of the blood sugar level of the patient within a desired range. For some applications, operator controls 71 enable the patient and/or healthcare provider to control various aspects of operation of gastric device 26.

In an embodiment of the present invention, control unit 90 employs an eating detection algorithm to detect eating by the patient, responsive to changes in one or more sensed parameters. The eating detection algorithm typically utilizes one or both of the following sub-algorithms for detecting eating: an impedance sub-algorithm and an electrical slow wave sub-algorithm. An increase in impedance is generally caused by stomach distension resulting from eating. A decrease in the rate of electrical activity in the antrum is generally caused by digestive activity resulting from the stomach filling with food.

Upon detection of an eating event, control unit 90 drives gastric device 26 to reduce a volume of stomach 20, so as to limit an ability of the patient to eat, because over-eating results in nausea, vomiting, and/or loss of appetite. Cessation of eating is typically determined by: (a) no longer detecting a particular indication of eating, and/or (b) running analogous algorithms to those described herein, but establishing different thresholds, indicative of, for example, reduction of fundic pressure or restoration of basal slow-wave rates. Upon identifying the cessation of eating, the control drives gastric device 26 to restore the original stomach volume, so as, for example, to prevent counterproductive remodeling of the stomach. Alternatively or additionally, upon detection of an eating event, control unit 90 applies:

the colonic stimulation techniques described hereinbelow with reference to FIGS. 9-11; and/or the hepatic portal vein stimulation techniques described in the above-mentioned U.S. Provisional Patent Application entitled, "Hepatic device for treatment, eating detection, and glucose level detection," filed on even date herewith.

Further alternatively or additionally, upon detection of an eating event, control unit 90 uses one or more techniques for appetite suppression known in the art, including, but not limited to:

activating an insulin pump;

activating a cholecystokinin (CCK) pump (which, for some applications, is performed to treat a metabolic or behavioral disorder, in the absence of some or all of the other techniques described herein);

stimulating the pancreas using techniques described in U.S. Pat. No. 5,919,216 to Houben et al., which is incorporated herein by reference; and stimulating the vagus nerve in order to modulate insulin secretion, such as described in U.S. Pat. Nos. 5,188,104, 5,231,988, and/or 5,263,480 to Wernicke et al., which are incorporated herein by reference.

The control unit is typically configured to invoke the eating detection algorithm periodically, e.g., by sampling once every 100 milliseconds. In an embodiment of the present invention, control unit 90 implements the eating detection algorithms and sub-algorithms as a state machine.

Control unit 90 is typically configurable to allow a healthcare worker to specify which of the sub-algorithms the eating detection algorithm utilizes. If the use of both sub-algorithms is specified, the control unit performs both of the sub-algorithms essentially simultaneously, e.g., by using two microprocessors, or, alternatively, by time-sharing a single microprocessor. In addition, in such a case, the control unit is typically further configurable to specify whether an indication from both sub-algorithms is required in order for the eating detection algorithm to determine that an eating event is occurring (i.e., a logical AND operation), or whether an indication from just one of the sub-algorithms is sufficient (i.e., a logical OR operation). If an AND operation is specified, the control unit is typically still further configurable to specify the required degree of synchrony between eating detection by the two sub-algorithms, as described hereinbelow with reference to FIG. 8.

Figure 5:
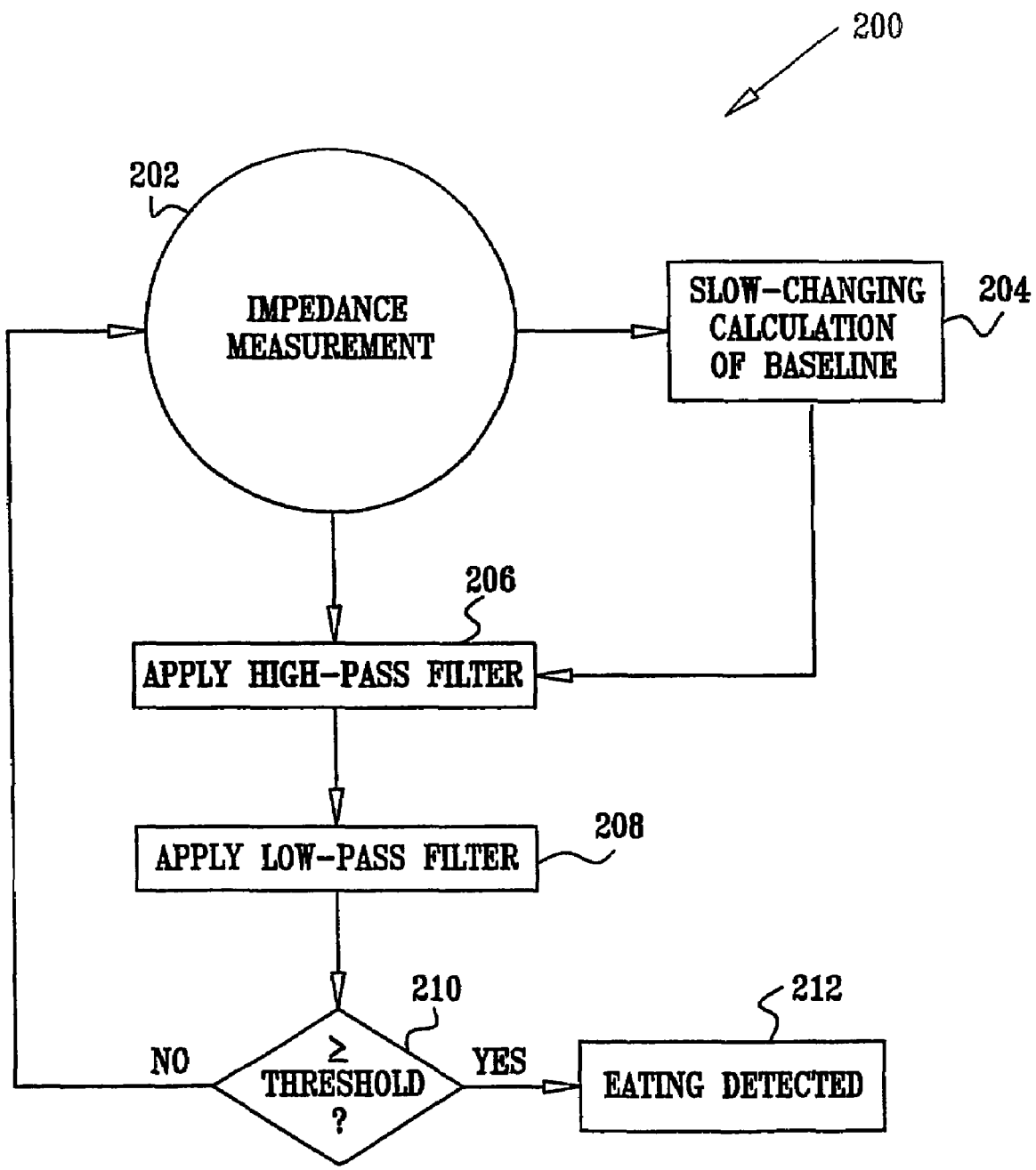
FIG. 5 is a flow chart illustrating an impedance sub-algorithm for detecting eating, in accordance with an embodiment of the present invention.

Reference is made to FIG. 5, which is a flow chart illustrating an impedance sub-algorithm 200 for detecting eating, in accordance with an embodiment of the present invention. Impedance sub-algorithm 200 has as an input an impedance measurement 202 generated by one or more local sense electrodes 74, which are typically placed on or in the fundus and/or the antrum of stomach 20 for this purpose (FIGS. 1-3). In this embodiment, local sense electrodes 74 comprise two or more electrodes through which a small current is driven. A simultaneous measurement of the resultant voltage drop yields the impedance. When local sense electrodes 74 have been placed on or in both the fundus and the antrum, the control unit is typically configurable to allow a healthcare worker to select whether the impedance from the fundus and/or the antrum is used. Impedance measurement 202 is generated and inputted into the sub-algorithm periodically, e.g., once every 100 ms. It is noted that although successive impedance measurements are generally described herein as being separated by 100 ms, this is by way of illustration and not limitation. For applications in which battery life is not a significant concern, measurement periods of every 10 ms may be used. Alternatively, for some applications, impedance measurements are carried out approximately once every 1-10 seconds.

Upon receipt of impedance measurement 202, sub-algorithm 200 uses the impedance measurement to calculate a baseline value of the impedance, at a baseline calculation step 204. Sub-algorithm 200 typically uses a slow-reacting formula for calculating the baseline value, in order to avoid having high frequency noise affect the calculation of the baseline. For example, the sub-algorithm may use the following equation to calculate and update the baseline value:

$$B=[B*(N1-1)+X]/(N1*N3)$$

where B is the baseline value (initialized to zero), N1 is a constant, e.g., 512, X is impedance measurement 202, and N3 is a configurable parameter, typically having a value between about 1 and about 10. For example, N3 may have a value selected from 1, 2, 4, and 8. Higher values of N3 result in slower convergences of B to the baseline.

Sub-algorithm 200 applies a high-pass filter to impedance measurement 202, by comparing the measurement to the baseline value, at a high-pass filter step 206. Typically, the sub-algorithm performs this comparison by subtracting the baseline value from impedance measurement 202, resulting in an impedance variance value, i.e., the extent to which the impedance measurement varies from the baseline. Upon initialization of sub-algorithm 200, the sub-algorithm may repeat step 204 for a certain number of periods, so as to obtain a reasonable convergence on the baseline value, prior to performing step 206 for the first time. For some applications, this repetition of step 204 is performed during each cycle through sub-algorithm 200.

At a low-pass filter step 208, sub-algorithm 200 applies a low-pass filter to the impedance variance value, resulting in a processed impedance value. This low-pass filtering serves to smooth variations in the impedance variance value, and to filter out spurious high values. For example, sub-algorithm 200 may use the following equation to perform the low-pass filtering:

$$S=[S*(2^{N4}-1)+\Delta X]/2^{N4}$$

wherein S is the processed impedance value (initialized to zero), N4 is a configurable parameter, typically having a value between about 1 and about 5, and $\Delta X$ is the impedance variance value. For example, N4 may have a value selected from 1, 2, 3, and 4. Higher values of N4 tend to reduce false positive indications of eating, while lower values tend to reduce false negatives. In general, any of the values 1-4 is suitable.

Sub-algorithm 200 compares the processed impedance value to a configurable threshold value, at a threshold check step 210. The threshold value typically is between about 2 and about 80 ohms. For example, the threshold value may be between about 30 and about 40 ohms when local sense electrodes 74 are placed about 2.5 cm apart, approximately 2 cm inferior to the gastroesophageal junction. Because the processed impedance value represents a difference between impedance measurement 202 and the baseline value, the threshold value is typically expressed as an absolute value (i.e., in ohms), rather than as a percentage change. If sub-algorithm 200 finds that the processed impedance value is greater than the threshold, the sub-algorithm generates an impedance condition signal, at an eating detected step 212. Otherwise, the sub-algorithm waits until a new impedance measurement 202 is generated, and repeats the method. (In embodiments of the present invention that include the AND synchrony techniques described hereinbelow with reference to FIG. 8, the sub-algorithm includes the current time ($t_Z$) with the impedance eating detection signal. In addition, when the sub-algorithm does not detect eating, the sub-algorithm generates a non-impedance condition signal, including the current time ($t_{Non\ Z}$).)

Figure 6:
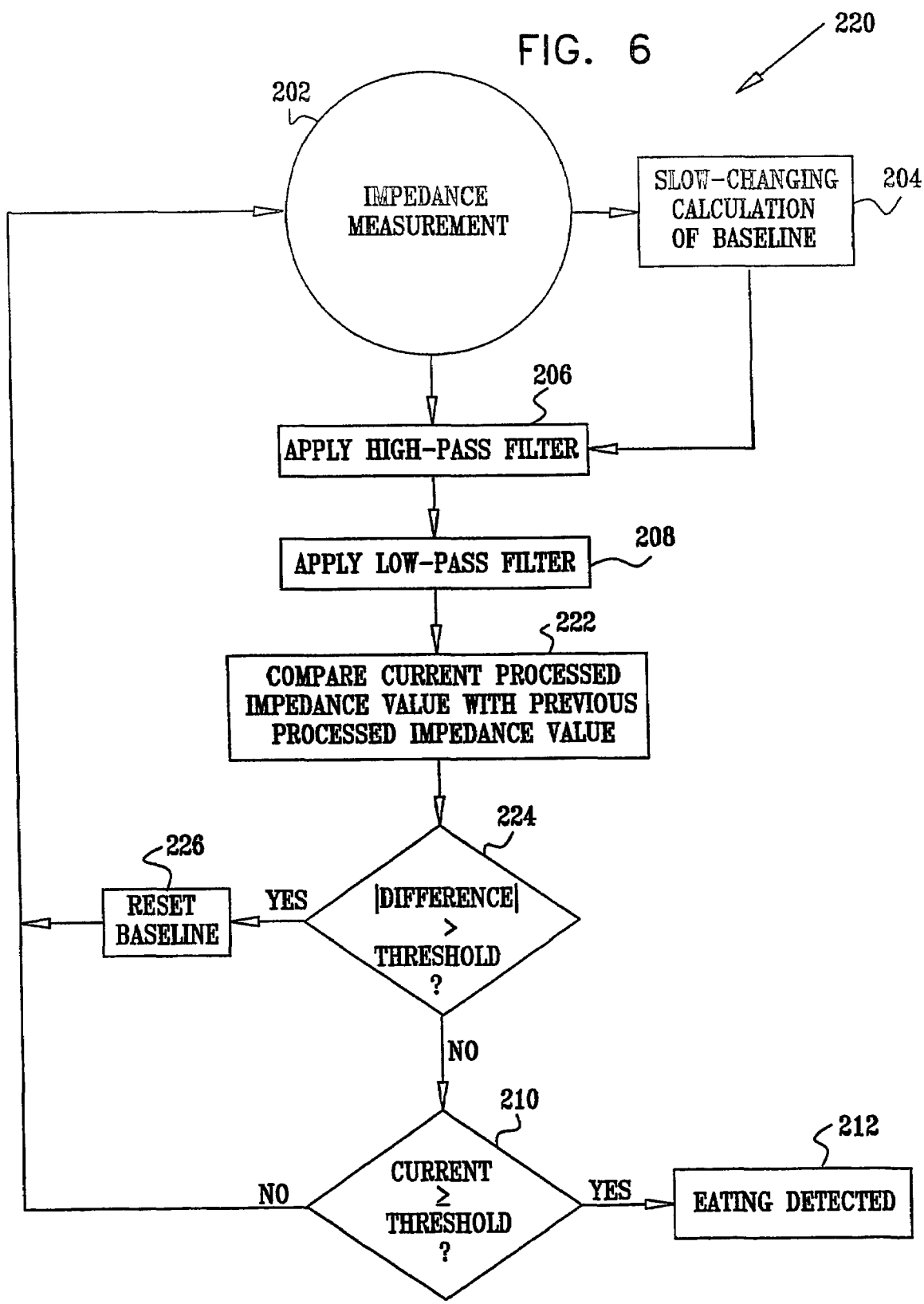
FIG. 6 is a flow chart illustrating another impedance sub-algorithm for detecting eating, in accordance with an embodiment of the present invention.

Reference is now made to FIG. 6, which is a flow chart illustrating an impedance sub-algorithm 220 for detecting eating, in accordance with an embodiment of the present invention. Impedance sub-algorithm 220 typically includes the same steps 204 through 212 as sub-algorithm 200. Sub-algorithm 220, however, contains additional steps, as described hereinbelow.

After applying the low-pass filter at step 208, as described hereinabove with reference to FIG. 5, sub-algorithm 220 compares the current processed impedance value received from the low-pass filter with a processed impedance value determined during a previous cycle through sub-algorithm 220, at a comparison step 222. The following equation expresses this comparison:

$$d=S_t-S_{t-N5}$$

where d is a difference between the current and previous processed impedance values, $S_t$ is the current processed impedance value, and $S_{t-N5}$ is the processed impedance value calculated based on the impedance measurement taken N5 periods earlier. As mentioned above, each measurement period may have a duration of 100 ms. For protocols having different measurement periods, N5 and other parameters may be suitably changed, mutatis mutandis. N5 is a configurable parameter, which typically has a value between about 1 and about 500 measurement periods, when such measurement periods have a duration of 100 ms. For example, N5 may have a value selected from 1, 5, 10, 20, 30, 50, 100, and 200 measurement periods.

The absolute value of the difference d is compared to a preconfigured threshold value, at a difference check step 224. If the difference is greater than the threshold, at a reset baseline step 226 sub-algorithm 220 resets the baseline value, by adding the current processed impedance value to the baseline value. (If the current processed impedance value is negative, such addition decreases the baseline value.) Sub-algorithm 220 waits until a new impedance measurement 202 is generated, and repeats the method. If, however, sub-algorithm 220 finds at step 224 that the difference is less than or equal to the threshold value, the sub-algorithm proceeds to check step 210, as described hereinabove with reference to FIG. 5.

For some applications, if N5 is greater than 1, sub-algorithm 220 performs check steps 224 and 210 only once per every N5 impedance measurements. Such reduced-frequency testing generally reduces power consumption and thus extends battery life of battery-operated implementations of gastric control apparatus 18.

The performance of steps 222, 224, and 226 may serve to reduce false detections of eating caused by changes in posture of the patient. Changes in posture sometimes cause sudden substantial changes in impedance measurement 202. Such changes in impedance are typically larger and more sudden than changes generally caused by the commencement of eating (and the resultant gradual increase in stomach volume), and generally continue as long as the patient maintains the new posture. By resetting the baseline value at step 226, sub-algorithm 220 incorporates the sudden change in impedance into the baseline value. Sub-algorithm 220 uses the reset baseline value for the high-pass filter at step 206, beginning with the next cycle through the algorithm. It is noted that any false negatives that may be caused by the performance of steps 222, 224, and 226 are generally transient The short delay before sub-algorithm 220 subsequently detects eating generally does not meaningfully affect the performance of gastric control apparatus 18.

Figure 7:
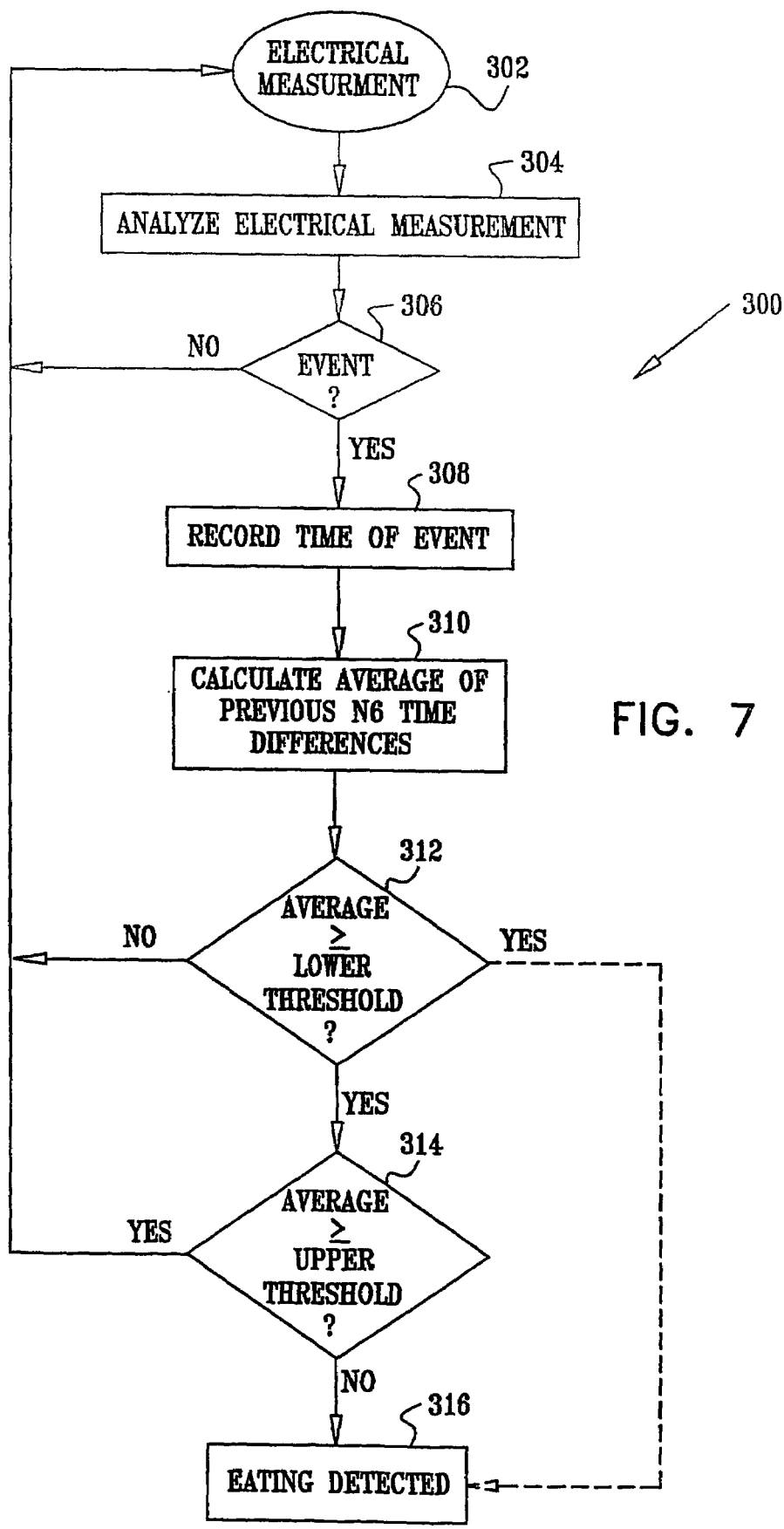
FIG. 7 is a flow chart illustrating an electrical slow-wave sub-algorithm for detecting eating, in accordance with an embodiment of the present invention.

Reference is now made to FIG. 7, which is a flow chart illustrating an electrical slow-wave sub-algorithm 300 for detecting eating, in accordance with an embodiment of the present invention. Slow-wave sub-algorithm 300 has as an input an electrical measurement 302 generated by one or more local sense electrodes 74 (FIGS. 1-3). In applications in which impedance is measured, as described hereinabove, these local sense electrodes 74 may be the same local sense electrodes 74 used for the impedance measurements, or may be separate therefrom. The sub-algorithm analyzes the electrical measurement, in order to determine whether an electrical event indicative of a slow wave has occurred, at an analysis step 304. Techniques known in the art for detecting slow waves may be utilized in analysis step 304. At an event check step 306, if the sub-algorithm does not detect an event, the sub-algorithm waits until another electrical measurement 302 is taken, and returns to the beginning of the method.

If, however, sub-algorithm 300 detects an event at step 306, the sub-algorithm records the time of the event, at a record time step 308. The sub-algorithm then calculates the time difference (lag) between the current event and the most recent previous event, and averages the most recent N6 time differences (including the current time difference), at an average calculation step 310. N6 typically has a value between about 1 and about 10; for example, N6 may be configurable to be selected from 1, 2, 4, and 6. Sub-algorithm 300 compares the average with a lower threshold value, which is typically between about 20 and about 30 seconds, at a lower threshold comparison step 312. In general, a decrease in the rate of electrical slow-waves in the antrum occurs during digestive activity caused by the stomach filling with food. Therefore, if sub-algorithm 300 finds that the average is greater than or equal to the lower threshold value, the sub-algorithm interprets such a finding as indicative of potential eating by the patient, and proceeds to an upper threshold comparison step 314, described below. On the other hand, if the sub-algorithm finds that the average is less than the lower threshold value, the sub-algorithm waits until another electrical measurement 302 is taken, and returns to the beginning of the method.

At upper threshold comparison step 314, sub-algorithm 300 compares the average time difference with an upper threshold value, which is typically between about 25 and about 80 seconds, e.g., between about 60 and 80 seconds. (The upper threshold value is typically between about 3 and about 4 times greater than the basal level of the time difference.) This comparison generally reduces false eating detections that may be caused by an occasional lack of detection of a slow wave by local sense electrodes 74. If sub-algorithm 300 finds that the average is less than the upper threshold value, the sub-algorithm generates a slow-wave condition signal, at an eating detected step 316. On the other hand, if the sub-algorithm finds that the average is greater than or equal to the upper threshold value, the sub-algorithm waits until another electrical measurement 302 is taken, and returns to the beginning of the method. For some applications, sub-algorithm omits step 314, and proceeds directly from step 312 to step 316 if the sub-algorithm finds that the average is greater than or equal to the lower threshold value. (In embodiments of the present invention that include the AND synchrony techniques described hereinbelow with reference to FIG. 8, the sub-algorithm includes the current time ($t_{Rate}$) with the slow-wave eating detection signal.)

In an embodiment, eating detection based on interpreting electrical activity of the stomach, as described hereinabove, is supplemented by or replaced by one or more of the following protocols:

Analysis of action potential propagation velocity within slow waves. Action potential propagation velocity is typically determined by measuring the duration of a slow wave. If, for example, the average basal duration of a slow wave is 5 seconds, then an increase of the duration by greater than about 7-15% (e.g., by 10% to 5.5 seconds) is interpreted as an indication of stomach distention or anticipation of imminent eating. A subsequent decrease in the duration towards the average basal duration is indicative of cessation of eating. Alternatively or additionally, changes in morphological features of the slow wave besides duration are analyzed to determine the onset and termination of eating.

Sensing antral contractions indicative of the onset or imminent onset of eating. An increased presence of sensed energy within a particular frequency band indicates that antral contractions are occurring, and are interpreted to indicate that eating has started or is about to start. For some applications, the energy band ranges from about 0.5 Hz to about 3 Hz, and is typically between about 1 and 2 Hz. Correspondingly, a decrease of sensed energy in the frequency band is interpreted to indicate cessation of eating.

Detecting ectopic sites of natural gastric pacing. When a sensed dysrhythmia is determined to initiate at an ectopic site, this is interpreted to indicate that the stomach is changing state (for example, filling or emptying).

Sensing efferent neural modulation of gastric electrical activity. The initiation of sensed electrical activity above about 5 Hz (e.g., between about 5 and 15 Hz) is interpreted to indicate the anticipation of imminent eating, or the onset of eating. Electrodes placed on the stomach detect this activity even when they are not placed directly on a nerve propagating the action potentials.

For some applications, multiple possible indications of eating are analyzed in combination, to increase the reliability of a determination by control unit 90 that eating is beginning. For example, if five possible indicators are evaluated, then a determination of eating may be made only if at least four out of five of the indicators are positive. In an embodiment, some of the indicators (e.g., changes in impedance and/or changes in the spacing between successive slow waves) are given a higher weight than the others.

Figure 8:
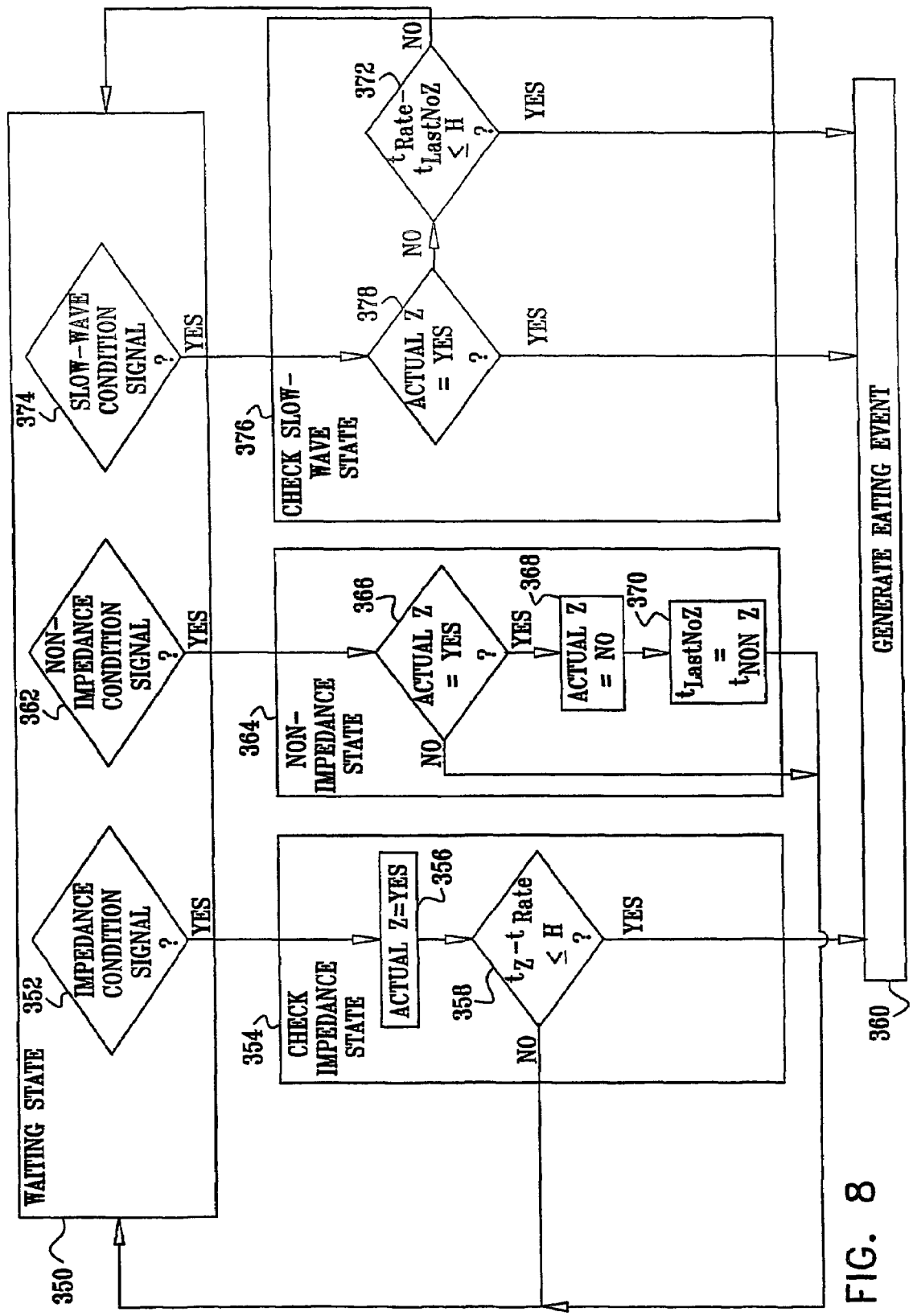
FIG. 8 is a block diagram that schematically illustrates states of a control unit during application of "AND synchrony," in accordance with an embodiment of the present invention.

Reference is made to FIG. 8, which is a block diagram that schematically illustrates states of control unit 90 during application of "AND synchrony," in accordance with an embodiment of the present invention. Control unit 90 typically implements these states when the control unit has been configured to utilize both the impedance and slow-wave sub-algorithms, and to combine the outputs from the two sub-algorithms using an AND operation with a required degree of synchrony. The control unit makes an eating determination only when the two sub-algorithms detect eating simultaneously or within a certain period of time from one another. Equivalent techniques for implementing AND synchrony will be evident to those skilled in the art who have read the present application, and are within the scope of the present invention.

The default state of control unit 90 is a waiting state 350. Upon initialization of this state, the control unit initializes the following variables (each of which is described hereinbelow): (a) Actual Z is set equal to NO, (b) $t_{LastNoZ}$ is set equal to negative infinity (or a number representative thereof, such as −32768), and (c) $t_{Rate}$ is set equal to negative infinity (or a number representative thereof, such as −32768). While in the waiting state, the control unit periodically or substantially constantly monitors whether sub-algorithms 200 and 220 generate signals, by performing the following three check steps substantially simultaneously, or by rapidly cycling through the following three check steps:

- At an impedance check step 352, control unit 90 checks for an impedance condition signal as generated at step 212, described hereinabove with reference to FIG. 5;
- At an impedance check step 362, control unit 90 checks for a non-impedance condition signal as generated as described hereinabove with reference to FIG. 5; and
- At a slow-wave check step 374, control unit 90 checks for a slow-wave condition signal, as generated at step 316, described hereinabove with reference to FIG. 7.

If the control unit detects an impedance condition signal at check step 352, the control unit transitions to a check impedance state 354. Upon entering check impedance state 354, control unit 90 sets an Actual Z flag equal to YES, at a set flag step 356. This flag indicates that an impedance condition is currently occurring. The control unit then subtracts $t_{Rate}$ (which is equal to negative infinity, until a value has been received together with a slow-wave signal as described hereinabove with reference to step 316 of FIG. 7) from $t_Z$ (which has been received together with the impedance condition signal, as described hereinabove with reference to step 212 of FIG. 5). At a synchrony check step 358, the control unit compares the resulting difference with a synchrony constant H, which is typically between 0 and about 300 seconds, e.g., 180 seconds. If the difference is less than H, indicating the control unit received impedance condition and slow-wave signals within H seconds of one another, the control unit generates an eating event, at an eating event generation step 360, and concludes the algorithm. On the other hand, if the control unit finds that the difference is greater than or equal to H, the control unit transitions back to waiting state 350.

While in waiting state 350, if the control unit detects a non-impedance condition signal at check step 362, the control unit transitions to a non-impedance state 364. If, at an Actual Z check step 366, the control unit finds that Actual Z equals YES, the control unit sets Actual Z to NO, at an Actual Z set step 368. In addition, at a $t_{LastNoZ}$ set step 370, the control unit sets $t_{LastNoZ}$ equal to $t_{Non\ Z}$, which was generated as described hereinabove with reference to FIG. 5. Thus, $t_{LastNoZ}$ now indicates the time when the most recent active impedance condition terminated. $t_{LastNoZ}$ is used as described hereinbelow with reference to a comparison step 372. The control unit then transitions back to waiting state 350.

While in waiting state 350, if the control unit detects a slow-wave condition signal at check step 374, the control unit transitions to a check slow-wave state 376. The control unit checks whether Actual Z equals YES, at an Actual Z check step 378. If the control unit finds that Actual Z does equal YES, indicating that the control unit has received the slow-wave condition signal during an active impedance condition, then the control unit generates an eating event, at eating event generation step 360, and concludes the algorithm On the other hand, if the control unit finds that Actual Z does not equal YES, the control unit checks whether $t_{Rate}-t_{LastNoZ}$ is less than H, at check step 372. If the control unit finds that $t_{Rate}-t_{LastNoZ}$ is less than H, indicating that the most recent impedance event concluded within H seconds of detection of the current slow-wave, then the control unit generates an eating event, at eating event generation step 360, and concludes the algorithm. Otherwise, the control unit transitions back to waiting state 350.

For some applications, control unit 90 drives gastric device 26 to reduce and/or restore the stomach volume according to a schedule, so as to induce reduction of the stomach volume at times when the patient might choose to eat but should not be eating, or when the patient's eating should be minimized. At other times, e.g., when the patient is sleeping, control unit 90 drives gastric device 26 to restore the stomach volume. Alternatively or additionally, control unit 90 (a) reduces the stomach volume during one or more meals during the day, so as to reduce the patient's appetite during those meals, and (b) restores the stomach volume during meals eaten during the remainder of the day, so as to prevent undesired side effects (e.g., nutritional deficiencies) which might occur in some patients from any inappropriate, excessive use of the stomach volume reduction techniques described herein.

Alternatively or additionally, the patient activates, deactivates, and modulates the level of stomach volume reduction in accordance with physician's instructions, aspects of the patient's diet, or other factors. For example, the patient may eat soup and salad at dinner, and then activate the control unit using operator controls 71, so as to increase the sense of satiety prior to being presented with a large selection of high-calorie options for an entree. The patient may subsequently input a command for a higher level of stomach volume reduction during dessert, such that the patient will feel very full, and, in fact, not have space for the dessert. It is seen through this example that this embodiment of the present invention can be used to encourage the patient to fully satisfy all nutritional needs, while simultaneously reducing or eliminating the hunger sensation which the patient would otherwise feel if stomach 20 were not in the reduced volume state caused by gastric device 26.

Reference is again made to FIG. 1. In this embodiment, the circumference of gastric band 32 is bidirectionally adjustable in real time responsive to input from control unit 90. The gastric band typically, but not necessarily, utilizes one or more of the following techniques for controllably adjusting the circumference thereof:

Gastric band 32 comprises a motor, such as a linear motor or a rotary motor, which is adapted to contract and expand gastric band 32. For example, motorized adjustment techniques may be used that are described in the above-referenced U.S. Pat. Nos. 6,067,991 and/or 6,454,699, and/or in the above-referenced US Patent Application Publications 2003/0066536 and/or 2001/0011543.

At least a portion of gastric band 32 comprises a temperature-sensitive material, the compliance and/or length of which varies in response to temperature changes. Control unit 90 applies changes in temperature to the material so as to achieve a desired stomach volume Gastric band 32 comprises a portion that is inflatable through a fill port. For example, an inner surface of the band may comprise the inflatable portion. Typically, the portion is inflated with a liquid, such as saline solution. The inflatable portion is typically connected by a tube to a balancing reservoir that is implanted under the skin of the patient. Band 32 further comprises a pump, which, responsive to input from control unit 90, transfers determined volumes of liquid in a closed circuit from the band to the reservoir or vice versa, to adjust the circumference of the band. For example, adjustable band inflation techniques may be used that are described in the above-referenced U.S. Pat. Nos. 5,938,669, 6,460,543, 6,453,907, and/or 6,454,699, and/or in the above-referenced US Patent Application Publications 2003/0066536 and/or 2001/0011543.

Alternatively or additionally, other techniques described in one or more of the publications referred to in the Background of the Invention are utilized for controllably adjusting the circumference of gastric band 32.

Reference is again made to FIG. 2. The volume of balloon 36 is bidirectionally adjustable in real time responsive to input from control unit 90. Typically, gastric balloon assembly 34 comprises a fluid reservoir 38 connected to balloon 36 by a tube 40. A valve 42, responsive to input from control unit 90, controls the amount of fluid introduced into or released from the balloon, in order to control the volume of the balloon, and thus the volume of stomach 20 remaining for containing food. For some applications, valve 42 comprises a pump. Adjustable balloon inflation techniques may be used that are described in the above-referenced U.S. Pat. No. 5,259,399. Alternatively or additionally, other techniques described in one or more of the publications referred to in the Background of the Invention are utilized for controllably adjusting the volume of balloon 36.

Reference is again made to FIG. 3. At least some of the sites to which electrodes 100 are applied are typically located on the body of the stomach, i.e., that portion of the stomach located between the lower-esophageal sphincter and the pyloric sphincter. The enhancement signal applied by electrodes 100 is typically configured so as to modulate contraction of muscles of the stomach and to thereby treat obesity. Typically, the enhancement signal includes, as appropriate, an Excitable-Tissue Control (ETC) signal and/or an excitatory signal which induces contraction of muscles of the stomach. Aspects of ETC signal application are typically performed in accordance with techniques described in the above-referenced PCT Publications WO 99/03533 and its corresponding U.S. national phase application Ser. No. 09/481,253, and/or U.S. Pat. No. 6,317,631 to Ben-Haim et al., mutatis mutandis. For some applications, the ETC signal is applied responsive to natural electrical activity of stomach 20, for example, after a designated delay following a detected activation of a portion of the stomach. For these applications, apparatus and methods may be used that are described in Israel Patent Application 129,257, entitled "Trigger-based regulation of excitable tissue control in the heart," mutatis mutandis. This application is assigned to the assignee of the present invention and is incorporated herein by reference.

Typically, control unit 90 drives electrodes 100 to apply the enhancement signal so as to create a contraction pattern of some of the muscles of stomach 20, in order to reduce the cross-sectional area of a portion 22 of the stomach. This reduction is believed to increase the sensation of satiety felt by the patient compared to that which was felt prior to application of the enhancement signal. Typically, the enhancement signal is configured such that the cross-sectional area of the stomach is reduced by at least 20%, and this reduction is maintained in one region of the stomach for a period of at least 1 minute. It is to be understood that for some applications, greater or lesser reductions in cross-sectional area may be desirable, and these may be maintained for periods greater or less than 1 minute.

Electrodes 100 typically comprise one or more signal application electrodes 30, which may also operate in a sensing mode. Electrodes 100 are typically coupled to the serosal layer of the stomach and/or inserted into the muscular layer of the stomach. Alternatively or additionally, the electrodes are coupled elsewhere on the stomach, gastrointestinal tract, or to other suitable locations in or on the body of the patient. The number of electrodes, as well as the positions thereof, are shown in FIG. 3 by way of example, and other sites on stomach 20 or in a vicinity thereof are appropriate for electrode placement in other applications of the present invention. Different types of electrodes known in the art are typically selected based on the specific manifestation of the patient's condition, and may comprise stitch, coil, screw, patch, basket, needle and/or wire electrodes, or substantially any other electrode known in the art of electrical stimulation or sensing in tissue.

For some applications, techniques described herein are performed in combination with techniques described in the above-referenced US Patent Application Publication 2002/0161414. For example, in embodiments of the present invention that comprise electrodes 100, control unit 90 may utilize the techniques described in the '414 patent application publication with reference to FIG. 2 thereof (regarding the operation of the control unit).

For some applications, electrodes 100 apply electrical stimulation in combination with the mechanical stomach volume modification techniques described hereinabove with reference to FIGS. 1 and 2. For example, electrical stimulation may be applied in order to achieve greater stomach volume reduction than is achievable by use of these mechanical techniques alone. In an embodiment, one or more of electrodes 100 is fixed to a surface of (a) gastric band 32 (FIG. 1) that comes in contact with tissue of stomach 20, such as the inner surface of gastric band 32, or (b) a surface of gastric balloon assembly 34 (FIG. 2) that comes in contact with tissue of stomach 20.

Figure 9:
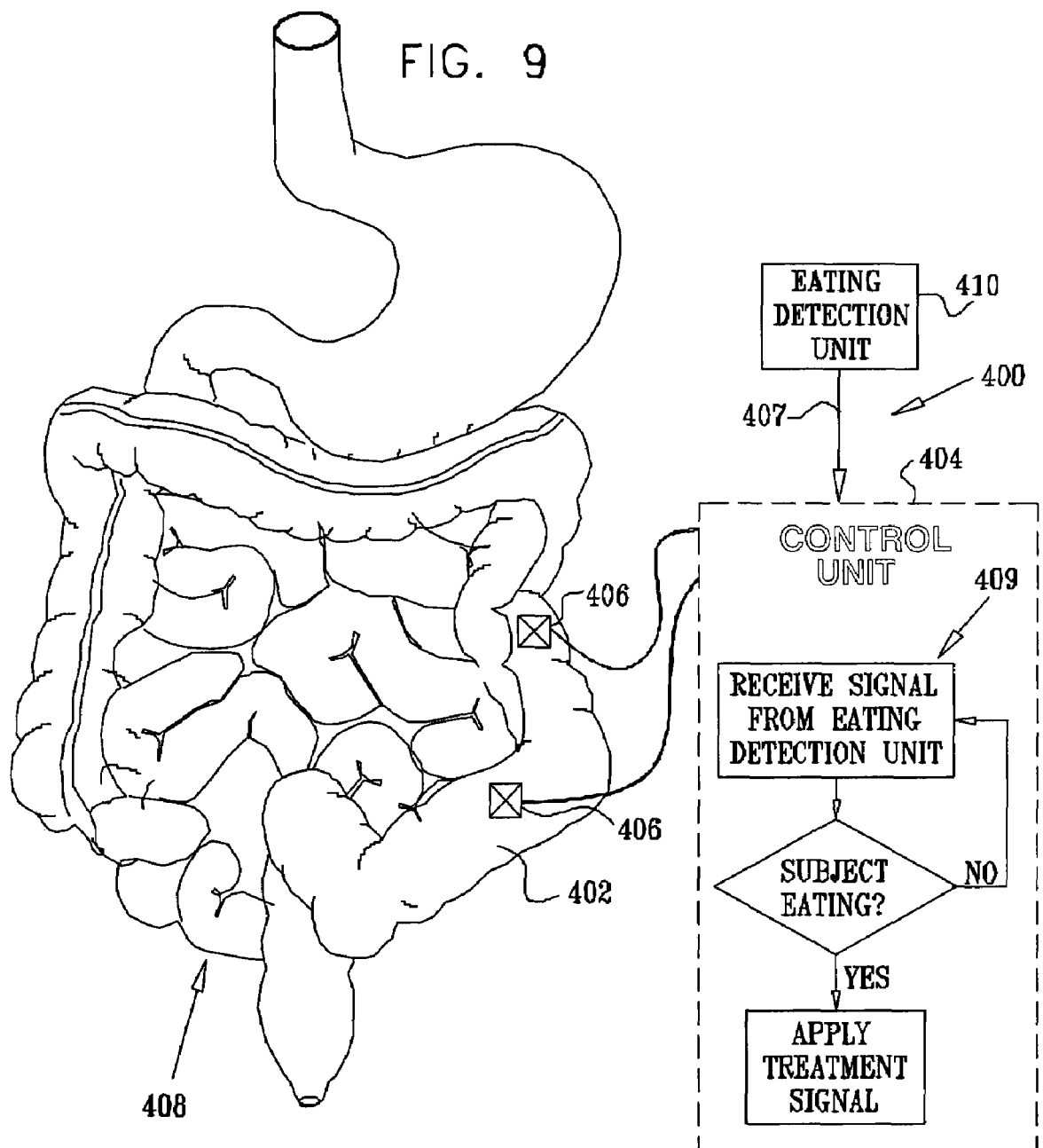
FIG. 9 is a schematic illustration of a colonic stimulation system applied to a colon of a patient, in accordance with an embodiment of the present invention.

Reference is now made to FIG. 9, which is a schematic illustration of a colonic stimulation system 400 applied to a colon 402 of a patient, in accordance with an embodiment of the present invention. System 400 comprises a control unit 404 and one or more electrodes 406, which are driven by control unit 404 to apply an electrical signal to respective sites on or in a vicinity of colon 402 or a distal small intestine 408 of the patient. Control unit 404 configures the signals to stimulate L-cells, which, responsive to such stimulation, increase secretion glucagon-like-peptide-1 (GLP-1). Such secretion of GLP-1 generally improves glycemic control of the patient, and therefore serves to treat patients suffering from insulin-resistance-related conditions, such as obesity, NIDDM, heart disease, and hypertension, or healthy patients considered at risk for such conditions. For some applications, techniques and apparatus described herein for increasing secretion of GLP-1 are adapted to, alternatively or additionally, increase secretion of peptide YY (PYY) or decrease secretion of ghrelin.

Using known calibration and optimization procedures, a range of suitable waveforms could be determined by a person of ordinary skill in the art who has read the disclosure of the present patent application. For some applications, the electrical signals are applied in bursts of pulses, where the frequency of the pulses within each burst is typically between about 1 and 200 Hz. In an embodiment, this frequency is between about 5 and 50 Hz. Each burst is typically spaced from a following burst by a spacing of approximately 1-10 seconds. For some applications, pre-selected parameters are fixed, or varied occasionally (for example, upon a visit to a physician). For other applications, the parameters are varied in real time. In one such application, detection of eating, excessive eating, or high glucose levels causes control unit 404 to increase the frequency of the pulses in each burst and/or to decrease the spacing between successive bursts.

In an embodiment, signals are applied to the colon using signal parameters described in the above-referenced PCT Patent Publication WO 99/03533 to Ben-Haim et al., entitled, "Smooth muscle controller," and U.S. patent application Ser. No. 09/481,253. In this embodiment, natural electrical activity of the colon is typically sensed, and an ETC signal is applied responsive thereto.

In an embodiment of the present invention, colonic stimulation system 400 further comprises an eating detection unit 410, which is adapted to detect eating by the patient and generate a detection unit signal 407 in response thereto. Control unit 404 is configured to drive electrodes 406 responsive to receiving detection unit signal 407, by running an algorithm 409. The control unit typically drives the electrodes to begin stimulation (a) substantially simultaneously with the commencement of eating, (b) between about one and about 5 minutes after the commencement of eating, or (c) between about one and about 5 minutes prior to commencement of eating. (Option (c) is possible because some of the techniques for eating detection described hereinbelow detect the anticipation of imminent eating.)

Eating detection unit 410 detects eating using (a) one or more of the techniques described hereinabove, (b) eating detection techniques known in the art, and/or (c) eating detection techniques described in one or more of the following patents and patent application publications:

the above-mentioned '414 patent application publication;
the above-mentioned PCT Publication WO 02/082968;
the above-mentioned US Provisional Patent Application entitled, "Hepatic device for treatment and eating detection," filed on even date herewith; and/or
the patents, patent application publications, and/or articles mentioned in the Background of the Invention section hereinabove.

In another embodiment of the present invention, control unit 404 is configured to drive electrodes 406 generally constantly, not responsive to detection of eating. Alternatively, the stimulation is applied periodically, such as once to several times an hour, during certain times of day or night, or in response to a command from the subject.

Figure 10:
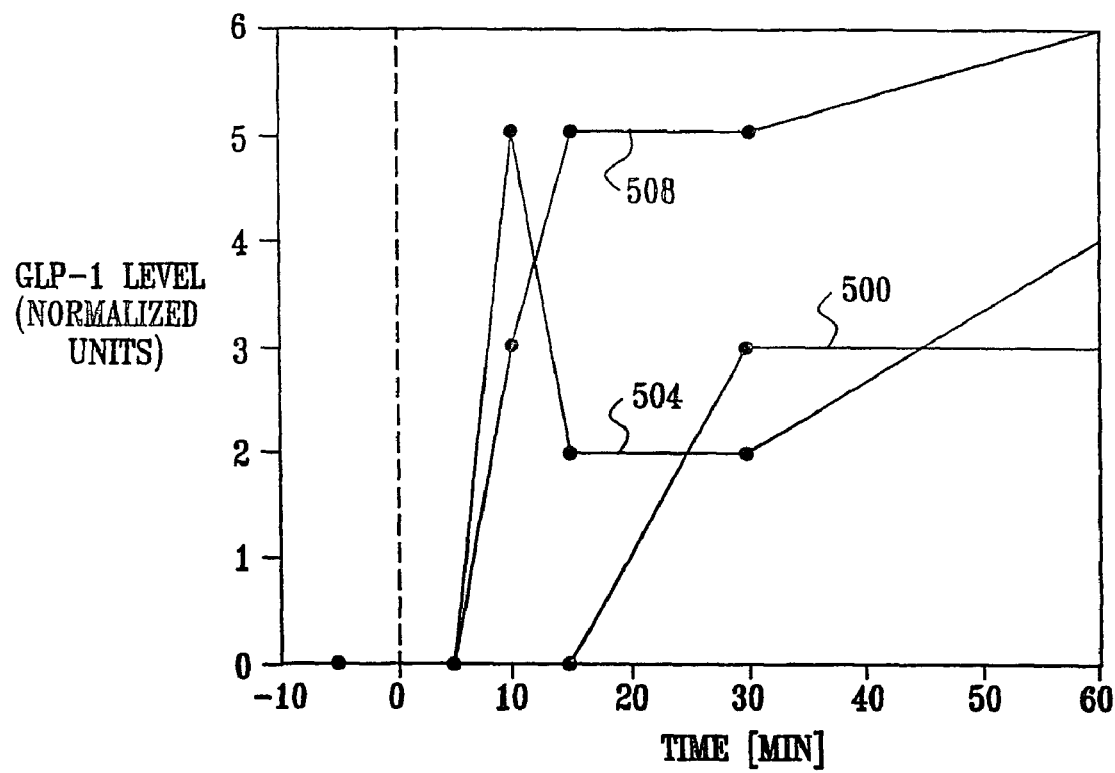
FIGS. 10 and 11 are graphs showing measurements of hormone levels taken during experiments performed in accordance with an embodiment of the present invention.
Figure 11:
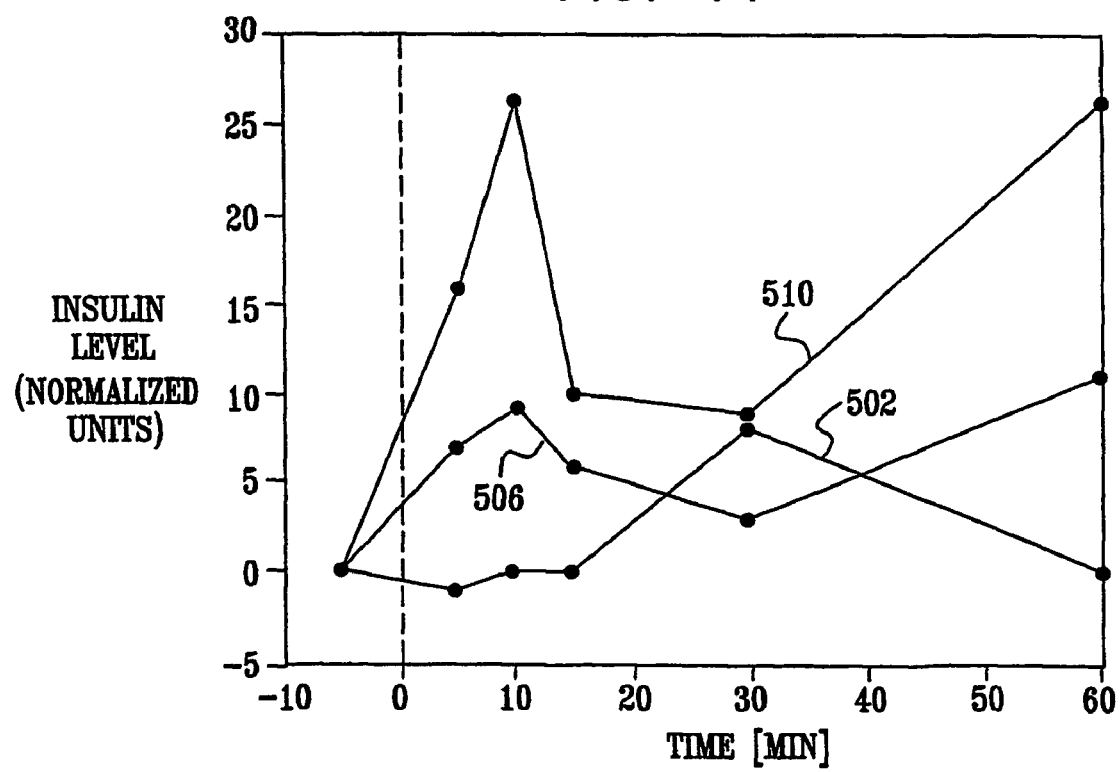

Reference is made to FIGS. 10 and 11, which are graphs showing measurements of hormone levels taken during experiments performed in accordance with an embodiment of the present invention. A single dog was anesthetized, and two pacing electrodes were implanted on an external surface of the distal colon of the dog. The electrodes were driven to apply non-synchronized stimulation with a sweep in parameters, ranging from 1 to 10 mA, at 5-200 Hz.

Measurements were taken on three separate days, each following twenty-four-hour fasting, while the dog was conscious. Stimulation was applied on two of these days, and the third day served as a control. On each of the days, eating began at time 0 and continued for about 10 minutes. The graphs in FIGS. 10 and 11 show GLP-1 levels and insulin levels, respectively, as measured during the same respective experiments on these three days. A line 500 (FIG. 10) and a line 502 (FIG. 11) show the measurements taken on the control day. The y-axis in each graph is labeled "normalized units." This indicates that the baseline values of GLP-1 and insulin (i.e., the measured values at T=−5 minutes) were subtracted from the respective data sets. Thus, the graphs show the increase from baseline of GLP-1 and insulin.

On the two stimulation days, stimulation was applied for 20 minutes beginning substantially simultaneously with the commencement of eating (at 0 minutes). A line 504 (FIG. 10) and a line 506 (FIG. 11) show the measurements taken on one of the stimulation days, while a line 508 (FIG. 10) and a line 510 (FIG. 11) show the measurements taken on the other stimulation day. As can be seen, there is a strong correlation between GLP-1 and insulin levels on all three days. Colonic stimulation enhanced GLP-1 and insulin peaks, and caused GLP-1 and insulin levels to rise earlier after the commencement of eating than occurred without such stimulation. In particular, GLP-1 and insulin levels had risen within 10 minutes of the onset of stimulation, while a measured response on the control day did not occur until 30 minutes after eating started.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a subject, comprising:
   applying an electrical signal to a site of the subject selected from the group consisting of: a colon of the subject, and a distal small intestine of the subject; and
   configuring the signal to stimulate cells of the subject to increase secretion of glucagon-like-peptide-1 (GLP-1), in order to treat the subject,
   wherein configuring the signal comprises:
      detecting an occurrence selected from the group consisting of an occurrence of eating, an occurrence of excessive eating, and an occurrence of an elevated blood glucose level; and
      responsive to detecting the occurrence, increasing a strength of the signal.

2. The method according to claim 1, wherein applying the signal comprises applying the signal in bursts of pulses, and wherein increasing the strength of the signal comprises increasing a frequency of the pulses in each of the bursts.

3. The method according to claim 1, wherein applying the signal comprises applying the signal in bursts of pulses, and wherein increasing the strength of the signal comprises decreasing a spacing between successive bursts.

4. A method for treating a subject, comprising:
   applying an electrical signal to a site of the subject selected from the group consisting of: a colon of the subject, and a distal small intestine of the subject;
   configuring the signal to stimulate cells of the subject to increase secretion of glucagon-like-peptide-1 (GLP-1), in order to treat the subject; and
   detecting eating by the subject, wherein applying the electrical signal comprises applying the signal responsive to detecting the eating.

5. The method according to claim 4, wherein the cells include L-cells, and wherein configuring the signal comprises configuring the signal to stimulate the L-cells to increase the secretion of the GLP-1.

6. The method according to claim 4, wherein the site includes the colon, and wherein applying the signal comprises applying the signal to the colon.

7. The method according to claim 4, wherein the site includes the distal small intestine, and wherein applying the signal comprises applying the signal to the distal small intestine.

8. The method according to claim 4, further comprising selecting a subject suffering from obesity, and wherein applying the signal comprises applying the signal to the site of the selected subject.

9. The method according to claim 4, further comprising selecting a subject suffering from a condition selected from the group consisting of NIDDM, heart disease, and hypertension, and wherein applying the signal comprises applying the signal to the site of the selected subject.

10. The method according to claim 4, wherein applying the signal comprises applying the signal periodically.

11. The method according to claim 4, wherein configuring the signal comprises varying at least one parameter of the signal in real time.

12. The method according to claim 4, wherein applying the signal comprises applying an excitable tissue control (ETC) signal to the site.

13. The method according to claim 12, comprising sensing natural electrical activity of the site, wherein applying the ETC signal comprises applying the ETC signal responsive to the sensed natural electrical activity.

14. The method according to claim 4, wherein applying the signal comprises applying the signal in bursts of pulses.

15. The method according to claim 14, wherein configuring the signal comprises configuring a spacing between successive bursts to have a duration of between about 1 and about 10 seconds.

16. The method according to claim 14, wherein configuring the signal comprises configuring a frequency of the pulses within each of the bursts to be between about 1 and about 200 Hz.

17. The method according to claim 16, wherein configuring the signal comprises configuring a frequency of the pulses within each of the bursts to be between about 5 and about 50 Hz.

18. The method according to claim 4, wherein applying the signal responsive to detecting the eating comprises commencing applying the signal at a time selected from the group consisting of substantially simultaneously with a commencement of the eating, between about one and about 5 minutes after the commencement of the eating, and between about one and about 5 minutes prior to the commencement of the eating.

19. The method according to claim 4, wherein detecting the eating comprises:
measuring an electrical impedance between two or more sites on a stomach of the subject, and generating an impedance signal responsive thereto;
detecting a change in posture of the subject by performing a posture analysis of the impedance signal;
detecting an indication of potential eating by the subject by performing an eating analysis of the impedance signal; and
responsive to the posture analysis, interpreting the impedance signal as indicative of the eating.

20. The method according to claim 4, wherein detecting the eating comprises:
measuring an electrical impedance between two or more sites on a stomach of the subject, and generating an impedance signal responsive thereto; comparing a measure of a sudden, sustained change in the impedance signal to a threshold; and
detecting the eating by analyzing the impedance signal, and responsive to the comparing.

21. The method according to claim 4, wherein detecting the eating comprises analyzing an electrical measurement of the stomach, and, responsive to the analysis, determining whether an electrical event indicative of a slow wave has occurred.

22. Apparatus for treating a subject, comprising:
at least one electrode, adapted to be coupled to a site of the subject selected from the group consisting of: a colon of the subject, and a distal small intestine of the subject;
a detection unit configured to detect an occurrence selected from the group consisting of: an occurrence of eating, an occurrence of excessive eating, and an occurrence of an elevated blood glucose level, and generate a detection unit signal in response thereto; and
a control unit, adapted to drive the at least one electrode to apply an electrical treatment signal to the site, and to configure the treatment signal to stimulate cells of the subject to increase secretion of glucagon-like-peptide-1 (GLP-1), in order to treat the subject, and
responsive to receiving the detection unit signal indicative of the detected occurrence, increase a strength of the treatment signal.

23. The apparatus according to claim 22, wherein the control unit is adapted to apply the treatment signal in bursts of pulses, and to increase the strength of the treatment signal by increasing a frequency of the pulses in each of the bursts.

24. The apparatus according to claim 22, wherein the control unit is adapted to apply the treatment signal in bursts of pulses, and increase the strength of the treatment signal by decreasing a spacing between successive bursts.

25. Apparatus for treating a subject, comprising: p1 at least one electrode, adapted to be coupled to a site of the subject selected from the group consisting of: a colon of the subject, and a distal small intestine of the subject;
a detection unit adapted to detect eating by the subject, and generate a detection unit signal in response thereto; and
a control unit, adapted to drive the at least one electrode to apply an electrical treatment signal to the site responsive to receiving the detection unit signal indicative of the detected eating, and to configure the treatment signal to stimulate cells of the subject to increase secretion of glucagon-like-peptide-1 (GLP-1), in order to treat the subject.

26. The apparatus according to claim 25, wherein the cells include L-cells, and wherein the control unit is adapted to configure the treatment signal to stimulate the L-cells to increase the secretion of the GLP-1.

27. The apparatus according to claim 25, wherein the site includes the colon, and wherein the control unit is adapted to apply the treatment signal to the colon.

28. The apparatus according to claim 25, wherein the site includes the distal small intestine, and wherein the control unit is adapted to apply the treatment signal to the distal small intestine.

29. The apparatus according to claim 25, wherein the control unit is adapted to configure the treatment signal to be suitable for treating a condition selected from the group consisting of obesity, NIDDM, heart disease, and hypertension.

30. The apparatus according to claim 25, wherein the control unit is adapted to apply the treatment signal periodically.

31. The apparatus according to claim 25, wherein the control unit is adapted to vary at least one parameter of the treatment signal in real time.

32. The apparatus according to claim 25, wherein to apply the treatment signal, the control unit is adapted to apply an excitable tissue control (ETC) signal to the site.

33. The apparatus according to claim 32, wherein the control unit is adapted to sense natural electrical activity of the site, and to apply the ETC signal responsive to the sensed natural electrical activity.

34. The apparatus according to claim 25, wherein the control unit is adapted to apply the signal in bursts of pulses.

35. The apparatus according to claim 34, wherein the control unit is adapted to configure a spacing between successive bursts to have a duration of between about 1 and about 10 seconds.

36. The apparatus according to claim 34, wherein the control unit is adapted to configure a frequency of the pulses within each of the bursts to be between about 1 and about 200 Hz.

37. The apparatus according to claim 36, wherein the control unit is adapted to configure the frequency of the pulses within each of the bursts to be between about 5 and about 50 Hz.

38. The apparatus according to claim 25, wherein to apply the treatment signal responsive to receiving the detection unit signal indicative of the detected eating, the control unit is adapted to commence applying the treatment signal at a time selected from the group consisting of substantially simultaneously with a commencement of the eating, between about one and about 5 minutes after the commencement of the eating, and between about one and about 5 minutes prior to the commencement of the eating.

39. The apparatus according to claim 25, wherein to detect the eating, the detection unit is adapted to:
   measure an electrical impedance between two or more sites on a stomach of the subject, and generate an impedance signal responsive thereto,
   detect a change in posture of the subject by performing a posture analysis of the impedance signal,
   detect an indication of potential eating by the subject by performing an eating analysis of the impedance signal, and
   responsive to the posture analysis, interpreting the impedance signal as indicative of the eating.

40. The apparatus according to claim 25, wherein to detect the eating, the detection unit is adapted to:
   measure an electrical impedance between two or more sites on a stomach of the subject, and generate an impedance signal responsive thereto,
   compare a measure of a sudden, sustained change in the impedance signal to a threshold, and
   detect the eating by analyzing the impedance signal, and responsive to the comparing.

41. The apparatus according to claim 25, wherein to detect the eating, the detection unit is adapted to analyze an electrical measurement of the stomach, and, responsive to the analysis, determine whether an electrical event indicative of a slow wave has occurred.

* * * * *